US 6,463,335 B1

(12) United States Patent
Münch et al.

(10) Patent No.: US 6,463,335 B1
(45) Date of Patent: Oct. 8, 2002

(54) TEMPORARY MEDICAL ELECTRICAL LEAD HAVING ELECTRODE MOUNTING PAD WITH BIODEGRADABLE ADHESIVE

(75) Inventors: Kuno Münch, Herzogenrath (DE); Marc Hendriks, Brunssum; Michel Verhoeven, Maastricht, both of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/518,352

(22) Filed: Mar. 3, 2000

Related U.S. Application Data

(63) Continuation-in-part of application No. 09/433,564, filed on Nov. 4, 1999, and a continuation-in-part of application No. 09/411,846, filed on Oct. 4, 1999, and a continuation-in-part of application No. 09/411,837, filed on Oct. 4, 1999.

(51) Int. Cl.$^7$ ................................................. A61N 1/00
(52) U.S. Cl. ..................................... 607/129; 600/374
(58) Field of Search ................................. 424/423, 426; 600/373, 374, 375; 607/116, 119, 126, 129, 130

(56) References Cited

U.S. PATENT DOCUMENTS

| 3,565,059 | A | | 2/1971 | Hauser et al. ............. 128/2.06 |
| 4,155,354 | A | | 5/1979 | Rasmussen ................. 128/640 |
| 4,282,866 | A | | 8/1981 | King |
| 4,298,598 | A | | 11/1981 | Schwarz et al. ............. 424/101 |
| 4,362,567 | A | | 12/1982 | Schwarz et al. ............. 106/157 |
| 4,377,572 | A | | 3/1983 | Schwarz et al. ............. 424/101 |
| 4,414,976 | A | | 11/1983 | Schwarz et al. ......... 128/334 R |
| 4,600,574 | A | | 7/1986 | Lindner et al. ................ 424/28 |
| 4,765,341 | A | * | 8/1988 | Mower et al. .............. 128/785 |
| 4,768,523 | A | | 9/1988 | Cahalan et al. |
| 4,804,691 | A | | 2/1989 | English et al. .............. 523/118 |
| 4,848,353 | A | | 7/1989 | Engel .......................... 128/640 |
| 4,900,554 | A | | 2/1990 | Yanagibashi et al. ........ 424/448 |
| 4,909,251 | A | | 3/1990 | Seelich ......................... 606/213 |
| 5,405,366 | A | | 4/1995 | Fox et al. ....................... 607/50 |
| 5,407,671 | A | | 4/1995 | Heimburger et al. ....... 424/94.1 |
| 5,412,076 | A | | 5/1995 | Gagnieu ....................... 530/356 |

(List continued on next page.)

OTHER PUBLICATIONS

"Autologous fibrin glue—preparation and clinical use in thoracic surgery"—European Journal of Cardio–thoracic Surgery (1992) 6: 52–54 (Kjaergard et al.).
"Important factors influencing the strength of autologous fibrin glue; the fibrin concentration and reaction time—comparison of strength with commercial fibrin glue"—Eur. Surg. Res. 1994; 26: 273–276 (Kjaergard et al.).
"Autologous fibrin glue for sealing vascular prostheses of high porosity"—Cardiovascular Surgery, Feb. 1994, vol. 2, No. 1: 45–47 (Kjaergard et al.).

(List continued on next page.)

Primary Examiner—Jeffrey R. Jastrzab
Assistant Examiner—Frances P. Oropeza
(74) Attorney, Agent, or Firm—Thomas F. Woods; Eric R. Waldkoetter; Tom G. Berry

(57) ABSTRACT

A temporary cardiac electrical stimulating lead is disclosed having a stimulating electrode mounted in or on an electrode mounting pad disposed at a distal end of the lead, the pad having a biodegradable adhesive disposed thereon and/or therewithin. The adhesive, and preferably also the electrode mounting pad, are capable of biodegradably dissolving over time in human body fluids. The adhesive permits the electrode mounting pad to be attached to a patient's epicardium without the use of sutures, or with fewer sutures than have heretofore been required to suitably affix an electrode mounting pad to a patient's heart. In a preferred embodiment, when the lead body is pulled away from the electrode mounting pad and removed from a patient, any portion of the electrode mounting pad and the adhesive remaining within the patient dissolves over time and disappears.

55 Claims, 10 Drawing Sheets

U.S. PATENT DOCUMENTS

| | | | |
|---|---|---|---|
| 5,459,177 A | 10/1995 | Miyakoshi et al. | 523/111 |
| 5,489,294 A | 2/1996 | McVenes et al. | |
| 5,496,872 A | 3/1996 | Constancis et al. | 523/118 |
| 5,522,888 A * | 6/1996 | Civerchia | 623/4 |
| 5,549,904 A | 8/1996 | Juergensen et al. | 424/423 |
| 5,552,452 A | 9/1996 | Khadem et al. | 522/63 |
| 5,605,541 A | 2/1997 | Holm | 604/82 |
| 5,643,596 A | 7/1997 | Pruss et al. | 424/426 |
| 5,691,152 A | 11/1997 | Burton et al. | 435/7.5 |
| 5,733,545 A | 3/1998 | Hood, III | 424/93.72 |
| 5,739,288 A | 4/1998 | Edwardson et al. | 530/382 |
| 5,750,657 A | 5/1998 | Edwardson et al. | 530/382 |
| 5,763,410 A | 6/1998 | Edwardson et al. | 514/21 |
| 5,763,411 A | 6/1998 | Edwardson et al. | 514/21 |
| 5,770,194 A | 6/1998 | Edwardson et al. | 424/94.64 |
| 5,773,418 A | 6/1998 | Edwardson et al. | 514/21 |
| 5,785,040 A | 7/1998 | Axelgaard | 128/640 |
| 5,804,428 A | 9/1998 | Edwardson et al. | 435/212 |
| 5,817,303 A | 10/1998 | Stedronsky et al. | 424/78.02 |
| 5,824,230 A | 10/1998 | Holm et al. | 210/749 |
| 5,849,033 A * | 12/1998 | Mehmanesh et al. | 607/129 |
| 5,883,078 A | 3/1999 | Seelich et al. | 514/12 |
| 5,900,245 A | 5/1999 | Sawhney et al. | 424/426 |
| 5,928,142 A | 7/1999 | Cartmell et al. | 600/372 |
| 5,936,035 A | 8/1999 | Rhee et al. | 525/54.1 |
| 5,942,406 A | 8/1999 | Burton et al. | 435/7.5 |
| 5,951,597 A * | 9/1999 | Westlund et al. | 607/126 |
| 5,961,484 A | 10/1999 | Gusakov et al. | 604/20 |
| 5,964,690 A | 10/1999 | Wright et al. | 494/12 |
| 5,964,724 A | 10/1999 | Rivera et al. | 604/4 |
| 6,200,587 B1 * | 3/2001 | Soe et al. | 424/423 |

OTHER PUBLICATIONS

"Preparation of autologous fibrin glue from pericardial blood"—Ann. Thorac. Surg. Feb. 1993; 55(2): 543–544 (Kjaergard et al.).

"Autologous fibrin glue—preparation and clinical use"—Ugeskr Laeger May 25, 1992; 154(22): 1554–1556 (Kjaergard et al.).

"Fibrin sealant: current and potential clinical applications"—Blood Coagulation and Fibrinolysis, vol. 7, 1996: 737–746 (Jackson et al.).

"Platelet gel as an intraoperatively procured platelet–based alternative to fibrin glue: program implementation and uses in noncardiovascular procedures"—The Proactive Hemostasis Management: The Emerging Role of Platelets Symposium, Jan. 23–24, 1997, Aspen, CO. (Green et al.).

"Clinical use of autologous platelet gel: hemostasis and wound healing"—The The Proactive Hemostasis Management: The Emerging Role of Platelets Symposium, Jan. 23–24, 1997, Aspen, CO. (Wilson).

"Autologous platelet gel in hepatic surgery"—The Proactive Hemostasis Management: The Emerging Role of Platelets Symposium, Jan. 23–24, 1997, Aspen, CO. (Beller et al.).

"Fibrin sealant: scientific rationale, production methods, properties, and current clinical use"—Vox Sang 1997; 72:133–143 (Radosevich et al.).

"Vivostat systems autologous fibrin sealant: preliminary study in elective coronary bypass grafting"—Ann. Thorac. Surg. 1998; 66: 482–6 (Kjaergard et al.).

"Platelet–rich plasma: growth factor enhancement for bone grafts"—Oral Surgery, Oral Medicine, Oral Pathology; vol. 85, No. 6: 638–646 (Marx et al.).

"Proocurement of autologous platelet rich gel"—www.perfusion.com/perfusion.articles (Stapleton et al.).

"Getting sticky in anti–adhesion?"—Biomaterials & Surgery—Nov.Dec. 1999: 169–171.

"A simple method of preparation of autologous fibrin glue by means of ethanol"—(Kjaergard et al.).

"The efficacy of autologous platelet gel (APG) in total knee arthroplasty"—American academy if Orthopedic Surgeons. 67th Annual Meeting Orlando, FL.

"Controlled Clinical Studies of Fibrin Sealant in Cardiothoracic Surgery –a Review" to H.K. Kjaergard et al. (Eur. J. Cardio–thorac. Surg. (1996) 10; 727–733.

* cited by examiner

TEMPORARY MEDICAL ELECTRICAL LEAD HAVING ELECTRODE MOUNTING PAD WITH BIODEGRADABLE ADHESIVE

RELATED PATENT APPLICATIONS

This patent application is a continuation-in-part of each of the following U.S. Patent Applications: (1) U.S. patent application Ser. No. 09/411,837 filed Oct. 4, 1999 entitled "Temporary Medical Electrical Lead Having Biodegradable Electrode Mounting Pad Loaded with Therapeutic Drug" to Lindemans et al. filed Oct. 4, 1999; (2) U.S. patent application Ser. No. 09/411,846 entitled "Temporary Medical Electrical Lead Having Biodegradable Electrode Mounting Pad" to van Wijk et al, filed Oct. 4, 1999; and U.S. patent application Ser. No. 09/433,564 filed Nov. 4, 1999 entitled "Biological Tissue Adhesives, Articles and Methods" to Hendriks et al. Each of the foregoing patent applications is incorporated by reference herein, each in its respective entirety.

FIELD OF THE INVENTION

The present invention relates to the field of cardiac stimulation, and more specifically to the field of stimulating cardiac tissue using a medical electrical lead.

BACKGROUND OF THE INVENTION

Atrial arrhythmias and supra ventricular tachycardias, such as atrial fibrillation, atrial flutter and atrio-ventricular re-entry, are common post-operative complications among heart surgery patients. It is estimated that during the first seven to ten days after cardiac surgery post-operative supra ventricular tachycardia occurs in up to 63 percent of patients. Aranki et al. showed that patients with postoperative atrial fibrillation have a mean hospital stay of about fifteen days, whereas those patients without post-operative atrial fibrillation have a mean hospital stay of about ten days. Whether such extended hospitalization stays are primarily caused by arrhythmias is not known. See Cardiac Surg. Kirklin J W, Barrat-Boyes BC (Eds.): NY 1993, pg. 210, "The Importance of Age as a Predicator of Atrial Fibrillation and Flutter after Coronary Artery Bypass Grafting", Leitch et al., J. Thorac. Cardiovasc. Surg., 1990:100:338–42; "Atrial Activity During Cardioplegia and Postoperative Arrhythmias", Mullen et al., J. Thorac. Cardiovasc. Surg., 1987:94:558–65.

The presence of such arrhythmias, which in otherwise healthy patients may not be unduly serious, may be especially harmful to heart surgery patients. The surgery itself, the effects of prolonged anesthesia, or both have often already compromised the hemodynamic condition of such patients. Drugs that might be used to prevent post-operative atrial fibrillation are often only partially effective and may have negative effects on cardiac pump function.

Supra ventricular tachycardias may further cause a very irregular ventricular rate, which in turn can lead to hemodynamic conditions deteriorating even further. Such deterioration is especially serious for patients having a compromised left ventricular function. Such complications may also present a serious impediment to the recovery of the patient. See, for example, "Maintenance of Exercise Stroke Volume During Ventricular Versus Atrial Synchronous Pacing: Role of Contractility", Ausubel et al., Circ., 1985:72(5):1037–43; "Basic Physiological Studies on Cardiac Pacing with Special Reference to the Optimal Mode and Rate After Cardiac Surgery", Baller et al., Thorac. Cardiovasc. Surg., 1981:29:168–73.

If post-operative atrial fibrillation proves to have unacceptable hemodynamic consequences or causes serious symptoms, and if it does not stop spontaneously or antiarrhythmic drugs are ineffective in treating it, external cardioversion or atrial defibrillation may be required. But external atrial defibrillation, although generally effective as a treatment, may have profound side effects. First, and in contrast to ventricular defibrillation where conversion to normal sinus rhythm may occur after the first shock, atrial defibrillation may not be obtained until after several shocks have been delivered to the patient. This is because ventricular contraction continues during supra ventricular tachycardia. Due to the large amounts of energy, which must be delivered in external defibrillation (e.g., 40 to 360 Joules), the shocks are not tolerated well by conscious patients. External defibrillation is therefore preferably performed under general anesthesia or at least when the patient is sedated. The use of anesthesia gives rise to yet another patient risk factor.

External defibrillation requires relatively high energy because the electrical source is not positioned directly upon the cardiac tissue and instead must pass through the thorax, which tends to dissipate the energy. In contrast, internally applied atrial defibrillation, such as may occur during surgery through defibrillation paddles placed directly on the heart, requires considerably less energy because the defibrillation electrical energy is applied only to the tissue that needs to be defibrillated. In fact, direct atrial defibrillation may be accomplished with only one-Joule pulses in contrast to the 40 Joule and greater pulses required for external defibrillation. See, for example, Kean D., NASPE abs. 246, PACE, April 1992, pt. II, pg. 570.

Defibrillation success rates generally depend on the amount of energy delivered. The lower amount of energy delivered, the lower the defibrillation success rate and the greater the number of shocks that must be applied to obtain successful defibrillation. By way of contrast, in direct atrial defibrillation, where energy is applied directly to the heart, the energy level can be selected such that the patient may more easily tolerate both the amount of energy delivered as well as the number of shocks required.

Waldo et al. in "Use of Temporarily Place Epicardial Atrial Wire Electrodes For The Diagnosis and Treatment of Cardiac Arrhythmias Following Open-Heart Surgery," J. Thorac. Cardiovasc. Surg., 1978, vol. 76, no. 4, pp. 558–65 disclose the use of a pair of temporary heart wires placed on the atrium to diagnose and treat arrhythmias through antitachycardia overdrive pacing. Temporary heart wires were sutured to the atrial walls at the time of the heart surgery. Once the patient was ready to be released from hospital, the wires were removed by traction or pulling upon the external end. See, for example, the temporary medical lead disclosed in U.S. Pat. No. 5,527,358 entitled "Temporary Medical Electrical Lead" to Mehmanesh et al.

Immobilization of mounting pads for electrical leads on the epicardium is currently accomplished by suturing the pad to the tissue, a potentially time-consuming process which can also cause damage to the patient's myocardial tissue. Moreover, when the electrode of a lead is removed, the sutures and mounting pad remain within the patient, or must be removed from the patient. When non-biodegradable pads or sutures are employed, a foreign body response is typically elicited from the patient's immune system. Such a response typically leads to scar tissue embedding the implanted electrode mounting pad or other components. The scar tissue may affect the performance of the patient's myocardial tissue. Thus, there exists a need to provide an improved temporary medical lead which may be attached to and removed from a patient's epicardium more quickly, which may be attached to and removed from the epicardium with less trauma occurring to a patient's cardiac tissue, and which provokes a less severe response form the human body.

Various devices, compositions and methods relating peripherally or directly to the present invention are described in the patents and technical papers listed in Tables 1 and 2 below.

TABLE 1

PATENTS

| U.S. Pat. No. | Inventors | Issue Date |
| --- | --- | --- |
| 5,964,724 | Rivera et al. | October 12, 1999 |
| 5,964,690 | Wright et al. | October 12, 1999 |
| 5,961,484 | Gusakov et al. | October 5, 1999 |
| 5,942,406 | Burton et al. | August 24, 1999 |
| 5,936,035 | Rhee et al. | August 10, 1999 |
| 5,928,142 | Cartmell et al. | July 27, 1999 |
| 5,900,245 | Sawhney et al. | May 4, 1999 |
| 5,883,078 | Seelich et al. | March 16, 1999 |
| 5,824,230 | Holm et al. | October 20, 1998 |
| 5,817,303 | Stedronsky et al. | October 6, 1998 |
| 5,804,428 | Edwardson et al. | September 8, 1998 |
| 5,785,040 | Axelgaard | July 28, 1998 |
| 5,773,418 | Edwardson et al. | June 30, 1998 |
| 5,770,194 | Edwardson et al. | June 23, 1998 |
| 5,763,411 | Edwardson et al. | June 9, 1998 |
| 5,763,410 | Edwardson et al. | June 9, 1998 |
| 5,750,657 | Edwardson et al. | May 12, 1998 |
| 5,739,288 | Edwardson et al. | April 14, 1998 |
| 5,733,545 | Hood, III | March 31, 1998 |
| 5,691,152 | Burton et al. | November 25, 1997 |
| 5,643,596 | Pruss et al. | July 1, 1997 |
| 5,605,541 | Holm | February 25, 1997 |
| 5,552,452 | Khadem et al. | September 3, 1996 |
| 5,549,904 | Juergensen et al. | August 27, 1996 |
| 5,496,872 | Constancis et al. | March 5, 1996 |
| 5,459,177 | Miyakoshi et al. | October 17, 1995 |
| 5,412,076 | Gagnieu | May 2, 1995 |
| 5,407,671 | Heimburger et al. | April 18, 1995 |
| 5,405,366 | Fox et al. | April 11, 1995 |
| 4,909,251 | Seelich | March 20, 1990 |
| 4,900,554 | Yanagibashi et al. | February 13, 1990 |
| 4,848,353 | Engel | July 18, 1989 |
| 4,804,691 | English et al. | February 14, 1989 |
| 4,600,574 | Lindner et al. | July 15, 1986 |
| 4,414,976 | Schwarz et al. | November 15, 1983 |
| 4,377,572 | Schwarz et al. | March 22, 1983 |
| 4,362,567 | Schwarz et al. | December 7, 1982 |
| 4,298,598 | Schwarz et al. | November 3, 1981 |
| 4,155,354 | Rasmussen | May 22, 1979 |
| 3,565,059 | Hauser et al. | February 23, 1971 |

TABLE 2

LITERATURE

| Authors | Title | Publication/Date |
| --- | --- | --- |
| Kjaergard et al. | Autologous fibrin glue - preparation and clinical use in thoracic surgery | European Journal of Cardio-thoracic Surgery (1992) 6: 52–54 |
| Kjaergard et al. | Important factors influencing the strength of autologous fibrin glue; the fibrin concentration and reaction time - comparison of strength with commercial fibrin glue | Eur. Surg. Res. 1994; 26:273–276 |
| Kjaergard et al. | Autologous fibrin glue for sealing vascular prostheses of high porosity | Cardiovascular Surgery, February 1994, Vol. 2, No. 1: 45–47 |
| Kjaergard et al. | Preparation of autologous fibrin glue from pericardial blood | Ann. Thorac. Surg. 1993 Feb; 55(2): 543–544 |
| Kjaergard et al. | Autologous fibrin glue - preparation and clinical use | Ugeskr Laeger 1992 May 25; 154(22): 1554–1556 |
| Jackson et al. | Fibrin sealant:current and potential clinical applications | Blood Coagulation and Fibrinolysis, Vol. 7, 1996: 737-746 |
| Green et al. | Platelet gel as an intraoperatively procured platelet-based alternative to fibrin glue: program implementation and uses in noncardiovascular procedures | The Proactive Hemostasis Management: The Emerging Role of Platelets Symposium, January 23–24, 1997, Aspen, CO. |
| Wilson | Clinical use of autologous platelet gel: hemostasis and wound sealing | The Proactive Hemostasis Management: The Emerging Role of Platelets Symposium, January 23–24, 1997, Aspen, CO |
| Beller et | Autologous platelet gel in hepatic surgery | The Proactive Hemostasis Management: The Emerging Role of Platelets Symposium, January 2314 24, 1997, Aspen, CO |
| Radosevich et al. | Fibrin sealant: scientific rationale, production methods, properties, and current clinical use | Vox Sang 1997; 72:133–143 |
| Kjaergard et al. | Vivostat systems autologous fibrin sealant: preliminary study in elective coronary bypass grafting | Ann. Thorac. Surg. 1998; 66:482–6 |
| Marx et al. | Platelet-rich plasma: growth factor enhancement for bone grafts | Oral Surgery, Oral Medicine, Oral Pathology; Vol. 85, No. 6: 638–646 |
| | The efficacy of autologous platelet gel (APG) in total knee arthroplasty | American Academy of Orthopaedic Surgeons: 67th Annual Meeting, Orlando, FL |

TABLE 2-continued

LITERATURE

| Authors | Title | Publication/Date |
|---|---|---|
| Stapleton et al. | Procurement of autologous platelet rich gel Getting sticky in anti-adhesion? | Www.perfusion.com/perfusion/articles Biomaterials & Surgery - Nov/Dec 1999: 169–171 |
| Kjaergard et al. | A simple method of preparation of autologous fibrin glue by means of ethanol | |

All patents and technical papers listed in Tables 1 and 2 hereinabove are hereby incorporated by reference herein, each in its respective entirety. As those of ordinary skill in the art will appreciate readily upon reading the Summary of the Invention, Detailed Description of the Preferred Embodiments and Claims set forth below, at least some of the devices and methods disclosed in the patents of Tables 1 and 2 may be modified advantageously in accordance with the teachings of the present invention. The foregoing and other objects, features and advantages, which will now become more readily apparent by referring to the following specification, drawings and claims, are provided by the various embodiments of the present invention.

SUMMARY OF THE INVENTION

The present invention has certain objects. That is, various embodiments of the present invention provide solutions to one or more problems existing in the prior art respecting conventional implantable pacing and/or defibrillation leads, including one or more of: (a) electrode mounting pad suturing times being excessive; (b) electrode mounting pad suture removal times being excessive; (c) damage or trauma occurring to a patient's myocardium, epicardium or pericardium as a result of attaching an electrode mounting pad to a patient's heart; (d) damage or trauma occurring to a patient's myocardium, epicardium or pericardium as a result of removing an electrode mounting pad from a patient's heart; (e) the requirement that a patient have an electrode mounting pad and corresponding medical lead surgically removed from within the patient's body after the lead and pad have served their purpose; (f) the cost, pain, time and trouble associated with removing a medical lead from within a patient's body.

Various embodiments of the present invention have certain advantages, including one or more of: (a) permitting lower defibrillation energy levels to be employed; (b) permitting fewer defibrillation pulses to be employed; (c) permitting temporary medical lead implantation surgical procedures to be completed more quickly; (d) reducing trauma or damage to a patient's pericardium, myocardium or epicardium; (e) improved physical and electrical coupling of the electrode mounting pad to a patient's pericardium, myocardium or epicardium; (f) eliminating the requirement that a patient have an electrode mounting pad and corresponding medical lead surgically removed from within the patient's body after the lead and pad have served their purpose; (g) eliminating the cost, pain, time and trouble associated with removing a medical lead from within a patient's body, and (h) being autologous.

Various embodiments of the present invention have certain features, including one or more of: (a) a collagen electrode mounting pad having a biodegradable adhesive attached thereto or loaded in at least portions thereof; (b) a biodegradable electrode mounting pad having a biodegradable adhesive attached thereto or loaded in at least portions thereof; (c) a non-biodegradable electrode mounting pad having a biodegradable adhesive attached thereto or loaded in at least portions thereof; (d) a method of making a biodegradable adhesive-loaded collagen electrode mounting pad and associated electrode; (e) a method of making a biodegradable adhesive-loaded biodegradable electrode mounting pad and associated electrode (f) a method of making a biodegradable adhesive-loaded non-biodegradable electrode mounting pad and associated electrode; (g) a collagen, biodegradable or non-biodegradable electrode mounting pad having a biodegradable adhesive attached thereto or loaded in at least portions thereof, where the adhesive dissolves and disappears within a patient's body after a pre-determined post-operative period of time has elapsed sufficient to permit the electrical stimulating function of the pad to have been performed; (h) a collagen or biodegradable electrode mounting pad having a biodegradable adhesive having a biodegradable adhesive attached thereto or loaded in at least portions thereof, where both the adhesive and the pad dissolve and disappear within a patient's body after a pre-determined post-operative period of time has elapsed sufficient to permit the electrical stimulating function of the pad to have been performed; (i) an electrode mounting pad having a biodegradable adhesive attached thereto or loaded in at least portions thereof which provides an improved degree of physical and electrical coupling of the pad to a patient's heart, and (j) a collagen, biodegradable or non-biodegradable electrode mounting pad having a biodegradable adhesive attached thereto or loaded in at least portions thereof, where the adhesive is autologous.

DESCRIPTION OF THE DRAWINGS

Other objects, advantages and features of the present invention will become apparent from the following specification, drawings and claims in which:

The drawings are not necessarily to scale. Like numbers refer to like parts or steps throughout the drawings.

DETAILED DESCRIPTION OF THE PREFERRED EMBODIMENTS

Figure 1:
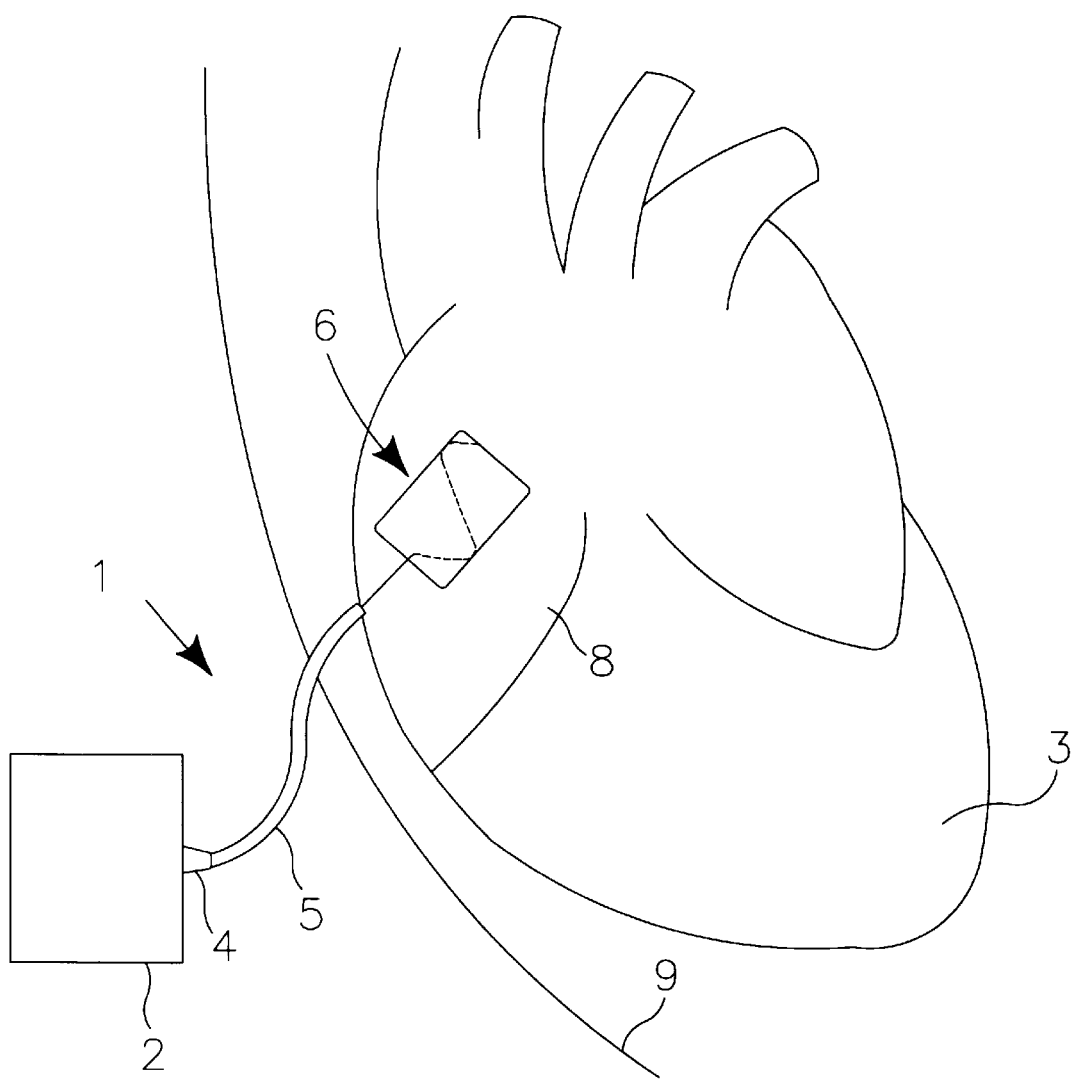
FIG. 1 shows a plan view of one embodiment of a lead of the present invention connected to an external pulse generator and a patient's heart.

FIG. 1 shows a plan view of one embodiment of lead 1 of the present invention. External pulse generator 2 is connected to patient's heart 3 by lead 1. Lead 1 comprises three sections: connector assembly 4, lead body 5 and electrode assembly 6. Typically two leads are attached to the heart: one to the left atrial wall and another to the right atrial wall. Defibrillation pulses are then delivered across the two electrodes through the left and right atria.

Connector assembly 4 connects lead 1 to external pulse generator 2, which may be, for example, an external pacemaker, external nerve or muscle stimulator, or an external defibrillator. Connector assembly 4 may be similar to any of several well known connector types disclosed in the prior art, such as the break-away needle connectors disclosed in U.S. Pat. Nos. 5,527,358, 5,871,528 and 5,792,217, all hereby incorporated by reference herein, each in its respective entirety. Connector assembly 4 may, for example, feature a break-away stainless steel needle having a recess which mates to a finger in a pin assembly. The break-away needle provided on the pin assembly permits the passage of connector assembly 4 from inside the body through the patient's skin to outside of the body. The break-away needle may thereafter be broken off at a breakpoint to permit the pin assembly to be connected to external pulse generator 2.

Alternatively, connector assembly 4 may comprise any of several types well known in the art suitable for electrically connecting the proximal end of lead 1 and the proximal end of electrical conductor 21 to implantable pulse generators (IPGs) such as implantable defibrillators, Implantable Pacer-Cardio-Defibrillators (PCDs), Implantable Cardio-Defibrillators (ICDs), implantable nerve stimulators, implantable muscle stimulators, implantable gastric system stimulators, and so on. That is, the lead of the present invention is not limited to use with external pulse generators only, but instead also finds application in conjunction with many types of implantable pulse generators.

Figure 2:
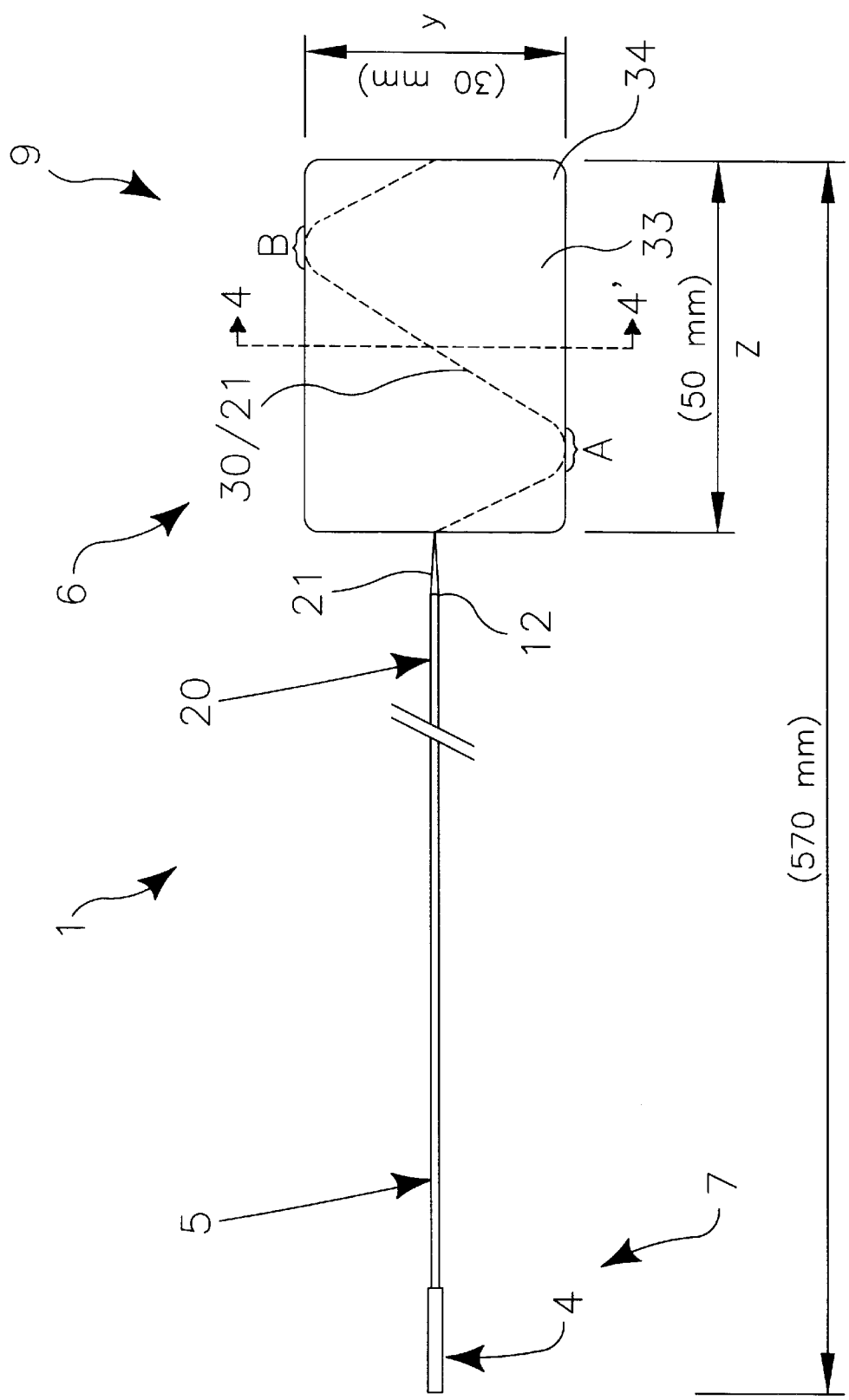
FIG. 2 shows a plan view of one embodiment of a lead of the present invention.

Referring now to FIG. 2, lead body 5 preferably comprises an insulative outer sleeve or sheath 20 having a central lumen, which encases one or more electrical conductors 21. Portions of the lumen forming unfilled gaps, such as gaps between one or more inner conductors 21, may be filled with medical adhesive. Outer sleeve 20 may be constructed from any suitable biocompatible (and preferably biostable) material such as FEP (fluorinated ethylene polymer), PTFE (polytetrafluoroethylene), PEBAX, TEFZEL, polyimide, PVDF (polyvinyldine fluoride), polyurethane, silicone rubber, or any other suitable material.

One or more inner conductors 21 are each constructed in a similar fashion. Thus, the construction of only one such conductor need be described. Inner conductor 21 preferably comprises a plurality of stranded wires, which form electrode wire 30. In a preferred embodiment of the present invention, inner conductor 21 is a multi-filament stainless steel stranded wire. It should be understood, of course, that any suitable material or wire may be employed to form conductor 21, including a coiled wire or any other type of wire made from an acceptable biocompatible material or metal including, but not limited to, such materials as platinum, palladium, titanium, tantalum, rhodium, iridium, carbon, vitreous carbon, and alloys, mixtures, combinations, oxides and/or nitrides of the foregoing. Of course, some materials are incompatible with others and may not be used effectively together. The limitations of specific electrically conductive materials for use with other electrically conductive materials in the context of implantation within the human body are well known in the art.

As best seen in FIG. 2, outer sleeve or insulation 20 terminates at location 12 near the distal end of lead 1. At least one electrical conductor 21 extends between proximal end 7 of lead 1 and distal end 9 of lead 1, and extends distally from the distal end of insulation 20 to terminate near or at distal end 9 of electrode assembly 6. Alternatively, a discrete electrode member may be crimped or otherwise attached to the distal end of at least one electrical conductor 21 and extend distally therefore for attachment to or positioning in or on electrode mounting pad 33. In either embodiment of the present invention, at least one electrical conductor 21 or the discrete electrode member forms an electrode or electrodes for providing electrical stimulation to a patient's heart tissue.

Although FIG. 2 shows only one electrical conductor attached to mounting pad 33, more than one such electrical conductor may be mounted or attached thereto. Note the semi-sinusoidal shape of the distal end of electrical conductor 21 in FIG. 2. Such a shape has been discovered to maximize the surface area of the heart that may be defibrillated by electrode 30 while still maintaining the ability of electrode 30 to be removed from pad 33 through the application of a non-excessive pulling force exerted upon the proximal end of lead 1 by a physician (more about which we say below).

Computer modeling and animal experiments confirmed the efficacy of the serpentine electrode configuration shown in FIGS. 1 and 2. Two acute animal experiments showed that the Defibrillation Thresholds (DFTs) obtained with a single wire serpentine electrode of the type shown in FIGS. 1 and 2 were equal to those obtained with a prior art temporary defibrillation lead having three wires or electrodes conforming generally to the lead disclosed in U.S. Pat. No. 5,527,358 discussed hereinabove. The single wire serpentine electrode of the present invention has the advantages of providing lower material costs, lower manufacturing costs, and being less invasive owing to the smaller diameter of the piercing needle, which it permits.

Figure 3:
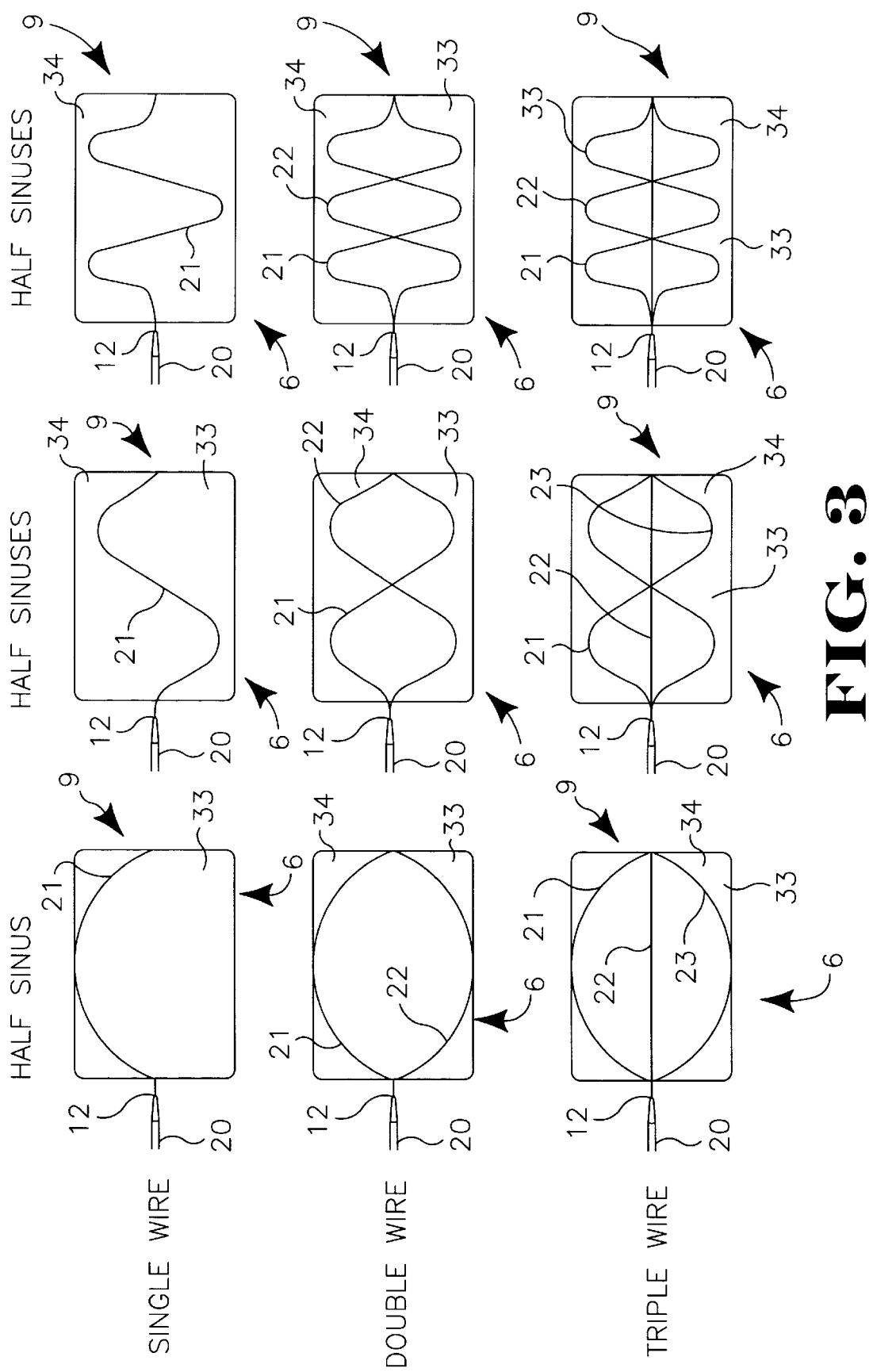
FIG. 3 shows plan views of various embodiments of the distal end of the lead of the present invention.

FIG. 3 shows several different embodiments of an electrode assembly that may be employed in conjunction with the present invention, including several embodiments where more than one electrical conductor or wire 21 is employed and attached to mounting pad 33. FIG. 3 shows electrical conductors 21, 22 and 23 arranged in various types of sinusoidal, curving or arcing configurations along mounting pad 33. It is to be noted, however, that the present invention is not limited in scope to embodiments having no more than three electrical conductors disposed on mounting pad 33, and specifically includes within its scope embodiments having more than three such electrical conductors. Additionally, the present invention is not limited in scope to embodiments where the one or more electrical conductors attached to mounting pad 33 assumes a sinusoidally-shaped, arced or curved configuration, but specifically includes within its scope embodiments having straight, triangular, rectangular, linear, non-curved, or non-arcing configurations. Electrode assembly 6 may assume any of several embodiments known in the art where more than one electrical conductor or wire 21 is employed and attached to mounting pad 33.

Figure 4:
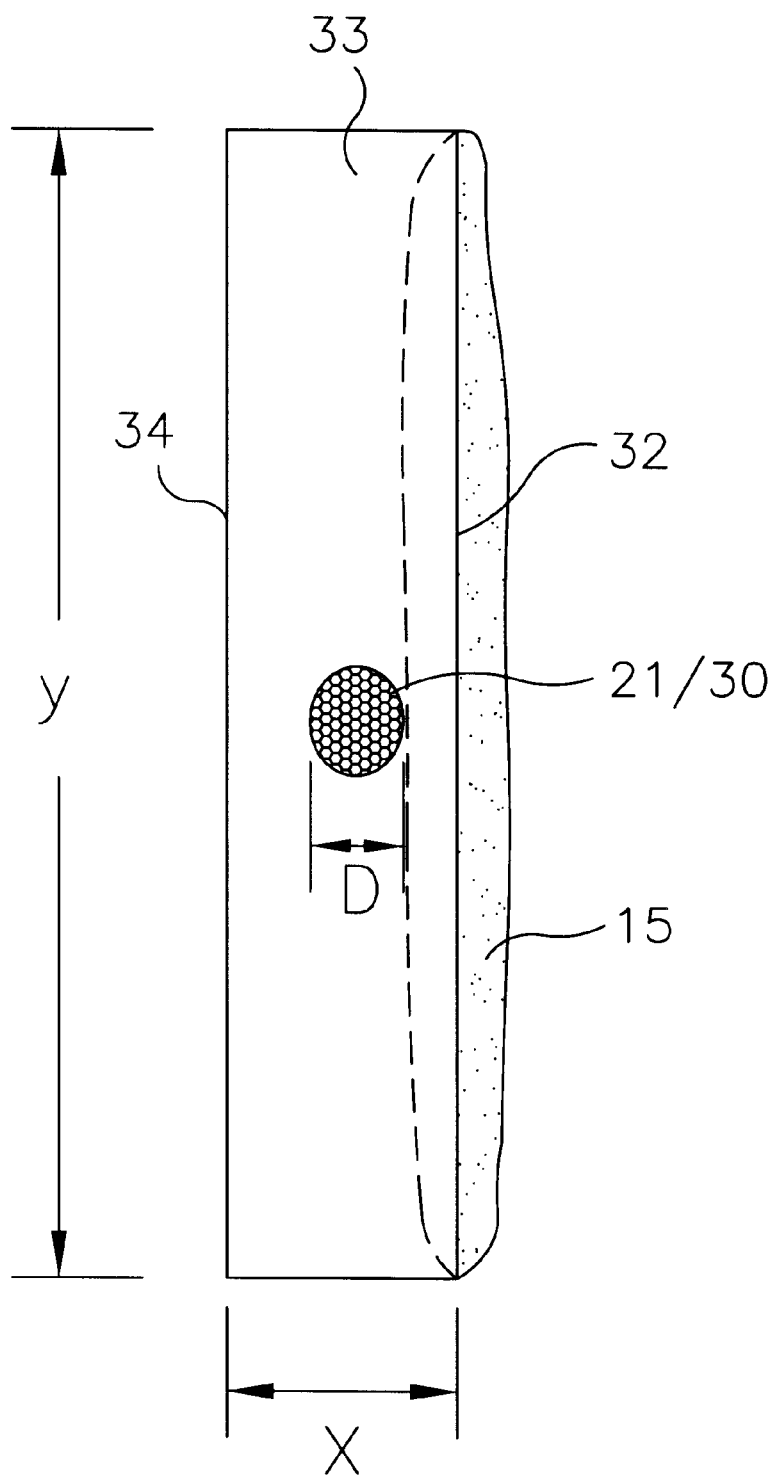
FIG. 4 shows a sectional view of the mounting pad and associated electrode of FIG. 2.

As noted above, electrode assembly 6 most preferably comprises one or more electrical conductors 21 and biocompatible, biostable mounting pad 33. The distal-most portion of each electrical conductor 21, 22 or 23 most preferably has a stranded metallic electrical conductor 30 exposed along the length of mounting pad 33. The distal end of electrical conductor 21 is most preferably disposed between opposing sides 32 and 34 of mounting pad 33, as shown in FIG. 4. In a preferred embodiment of the present invention, electrical conductor 21 is formed of about 49 individual medical grade stainless steel wires which are stranded together to form conductor 21 having a nominal diameter D of about 0.4 mm (see FIG. 3). In less preferred embodiments of the present invention, the wires may be braided or twisted together to form conductor 21.

Continuing to refer to FIGS. 2 and 4, thickness X of mounting pad 33 most preferably ranges between about 2 mm and about 3 mm, but may also range between about 1 mm and about 4 mm, or between about 0.5 mm and about 5 mm. Other thicknesses X and corresponding thickness ranges of mounting pad 33 are also contemplated in the present invention. Mounting pad length Z is most preferably about 50 mm, but may be any other suitable length. Likewise, mounting pad width Y is most preferably about 30 mm, but may be any other suitable width.

Referring now to FIG. 4, there is shown a partial cross-sectional view of pad 33 with electrical conductor 21/electrode wire 30 disposed therewithin. Bottom surface 32 of pad 32 is preferably configured for attachment to and engagement with a patient's a patient's pericardium, myocardium or epicardium of heart 3. Biodegradable adhesive 15 of the present invention, more about which we say below, is shown disposed on at least portions of bottom surface 32. As illustrated in FIG. 4, in a preferred embodiment of the present invention adhesive 15 impregnates or is pushed, loaded or otherwise disposed at least partially into pad 33 such that adhesive 15 physically extends beyond bottom surface 32. Biodegradable adhesive 15 may comprise any of a number of different compositions, some of which are discussed in detail below.

Adhesive 15 is capable of bonding pad 33 to patient's heart 3 without requiring the use of sutures or other attachment devices or methods. That is, adhesive 15 provides the requisite degree or bulk of physical attachment required to permit pad 33 to remain attached to patient's heart 3 for a sufficiently long period of time such that the pacing or defibrillation functions of lead 1 may be carried out successfully. Adhesive 15 also provides at least a portion of the requisite degree of electrical coupling required to permit electrical conductor 21/electrode wire to pace or defibrillate patient's heart 3 for a sufficiently long period of time such that the pacing or defibrillation functions of lead 1 may be carried out successfully.

It is a feature of the present invention that adhesive 15 be formed of a biodegradable material which breaks down over time and dissolves in the body fluids of the patient in which lead 1 has been implanted. Adhesive 15 is most preferably formed of a biocompatible material which remains substantially intact and retains sufficient adhesive characteristics for a period of time sufficient to permit lead 1 to have performed its desired functions (e.g., pacing and defibrillating the patient's heart for the required or desired period of time following the implantation procedure). In an even more preferred embodiment of the present invention, adhesive 15 and pad 33 are both formed of biocompatible materials which remain substantially intact for a period of time sufficient to permit lead 1 to have performed its desired functions (e.g., pacing and defibrillating the patient's heart for the required or desired period of time following the implantation procedure). In such an embodiment, only wire 30/conductor 21 and lead body 20 do not biodegrade and are removed form the patient by merely pulling them through the exit site of lead 1. Once the electrode and lead have been explanted and removed from the patient (which typically occurs anywhere between one day to two weeks following the operation in which the lead was initially implanted), mounting pad 33 and adhesive 15 most preferably begin to dissolve and break down or otherwise dissociate, thereby losing structural integrity.

In the preferred embodiments of the present invention shown in the drawings hereof, one or more inner conductors 21 is shown mounted within mounting pad 33. It should be understood that such inner conductors may be mounted to mounting pad 33 in any acceptable manner including, without limitation, suturing or gluing all or some of inner conductor 21 to outer surfaces 32 or 34 of mounting pad 33. Holes may further be provided in mounting pad 33, either for the purpose of exposing certain portions of conductor 21 to heart tissue or reducing the mass of pad 33. Thus, when electrode assembly 6 is attached to cardiac tissue, intermittent sections of the one or more conductors are directly exposed to cardiac tissue through such holes. Mounting pad 33 may further feature suture areas or portions disposed near the corners of pad 33 which permit at least portions of mounting pad 33 to be sutured directly to heart 3, as best seen in FIG. 1. That is, biodegradable adhesive 15 of the present invention may also be employed with sutures to secure mounting pad 33 to patient's heart 3.

In one embodiment of the present invention, mounting pad 33 is constructed and formed from collagen, but may alternatively be fashioned from any suitable biodegradable, biostable, pliant material (more about which we say below). It is a particular advantage of the collagen embodiment of the mounting pad of the present invention that when mounting pad 33 is formed from an appropriate collagenous material, mounting pad 33 dissolves or otherwise dissociates over time following implantation within the human body. Consequently, even after electrode 30/inner conductor 21 is removed or explanted from a patient's body, mounting pad 33 remains implanted within the patient but then disappears over time as it dissolves in the human body fluids within which it is implanted. Mounting pad 33 is most preferably formed of a collagenous material that maintains its structural integrity long enough to permit the post-operative defibrillation function of lead 1 to be carried out. Once the electrode and lead have been explanted and removed from the patient (which typically occurs anywhere between one day to two weeks following the operation in which the lead was initially implanted), mounting pad 33 most preferably begins to dissolve and break down or otherwise dissociate, thereby losing its structural integrity.

Collagen is a natural biopolymer material well suited for use in forming the biodegradable, biocompatible, electrode mounting pad of the present invention. Collagen is the principal structural protein in mammals, constituting approximately one-third of the total body protein. As the chief structural protein of the body, collagen is capable of transmitting tensile and compressive forces of great magnitude. In light of the application of the present invention, such properties are highly desirable. After implantation, a collagen electrode mounting pad of the present invention is enzymatically degraded through the cleavage of peptide bonds by human collagenase. In a preferred embodiment of the present invention, the degradation rate of collagen is controlled by means of crosslinking. Crosslinking may also be employed to enhance the mechanical properties of the electrode mounting pad (more about which we say below), and furthermore beneficially diminishes the antigenicity of the electrode mounting pad.

Other biodegradable, biocompatible materials suitable for use in forming the electrode mounting pad of the present invention include natural materials and their corresponding synthetic equivalents or derivatives, such as albumin, silk, poly(L)lysin, fibrin, elastin, hyaluronic acid preparations, and salts and derivatives thereof such as those described in U.S. Pat. No. 5,128,326, glycos-amino-glycans, polysaccharrides, keratin, chondroitin sulfates, dermatan sulfate, keratan sulfate, heparan, heparan sulfate, heparan substitutes, heparin, heparin substitutes, cellulose and its derivatives, starch, gelatin, dextrans and their derivatives, chitin, chitosan, and combinations or mixtures of, or the products of reactions involving, the foregoing.

Still other natural and synthetic biodegradable, biocompatible materials suitable for use in forming the electrode mounting pad of the present invention include, but are not limited to, aliphatic polyesters, polyamides, polyesteramides, polyorthoesters, polyanhydrides, polyphosphazenes, Poly(glycolic acid), Poly(L-lactic acid), Poly(DL-lactic acid), Poly(p-dioxanone), Poly(,-caprolactone), Poly(3-hydroxypropionic acid), Poly(3-hydroxybutyric acid), Poly( alpha-malic acid), Poly(beta-malic acid), Poly(serine ester).

Yet other natural and synthetic biodegradable, biocompatible materials, whether existing presently or in future, will surely find application and suitability in forming a biodegradable, biocompatible electrode mounting pad or adhesive of the present invention.

An electrode mounting pad comprising collagen was constructed using collagen pads obtained from Coletica, a company based in Lyon, France. Those pads were similar to a hemostatic sponge marketed by Coletica in France, Spain and Italy under the mark "HEMOSTAGENE" and distributed in the U.S. by MedChem Products, Inc. under the marks "AVIFOAM" and "ACTIFOAM." Note that the pads provided by Coletica had been prepared by suspending collagen in an appropriate solution, pouring the suspension solution into a 6 cm×6 cm metal cast, freezing and freeze-drying the solution contained within the cast, and pressing the resulting freeze-dried sponge to a thickness of 3 mm between plates heated to 80 degrees Celsius for 30 seconds at a pressure of 180 bars. Thereafter the pads were cut to appropriate size.

In a pre-clinical experiment, impedance measurements were performed to determine the conductivity of the collagen pad. Three different devices were compared: (1) Medtronic Model No. 13004 lead with PTFE electrode mounting pad; (2) Medtronic Model No. 13004 lead with bare wires and no electrode pad, and (3) Medtronic Model 13004 lead with collagen electrode mounting pad. The tested electrodes were positioned in a water bath containing a 0.9% saline solution at room temperature. Electrical shocks were applied between the test electrodes and a Medtronic Model No. 6721M epicardial patch electrode. The distance between the electrodes was set at 49 cm. For the delivery of the electrical shocks a Medtronic DISD Model No. 5358 and a Medtronic Model No. 9790 programmer were employed.

Figure 5:
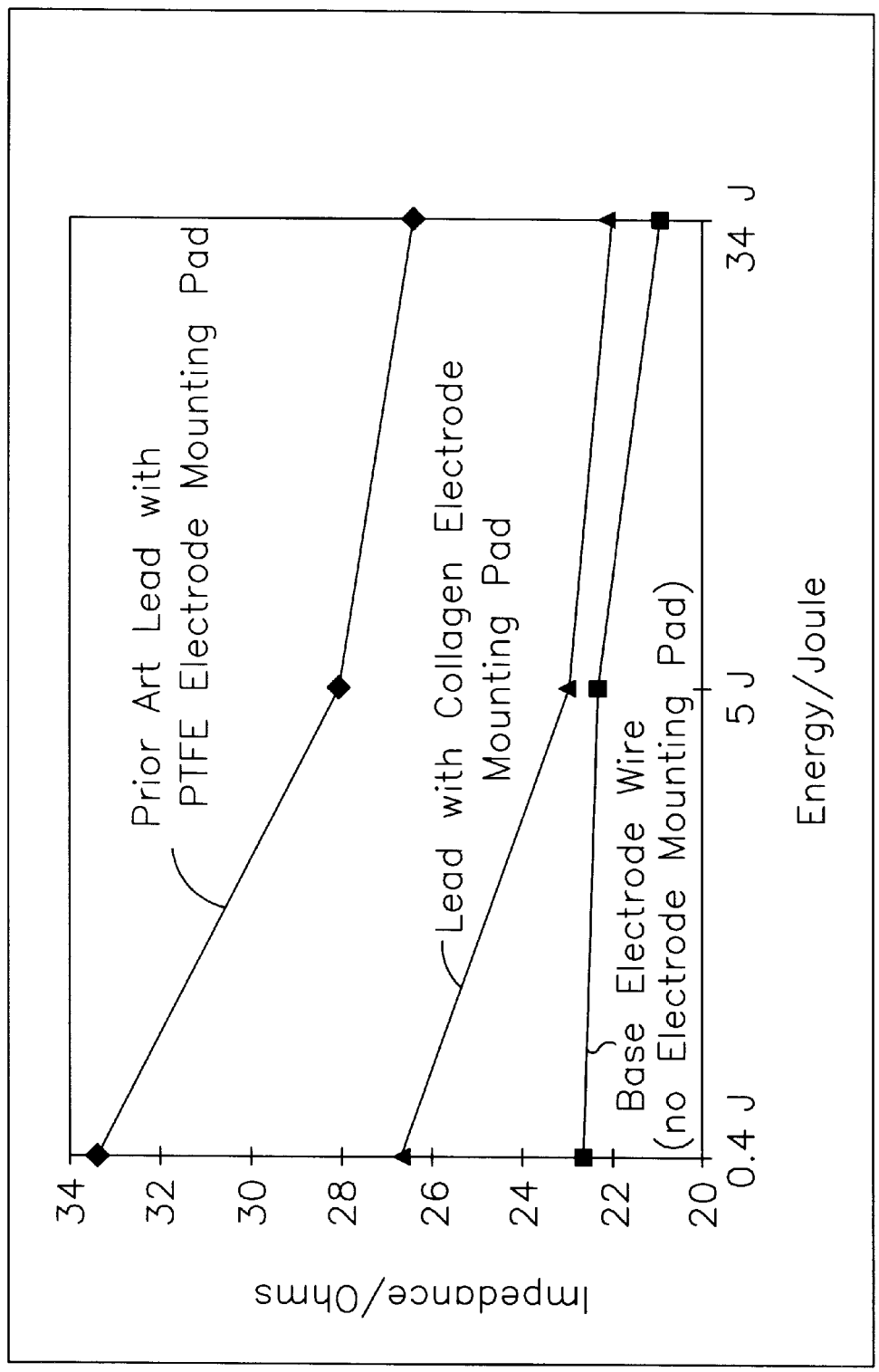
FIG. 5 shows comparative impedance versus energy data for a lead of the present invention and two prior art leads.

Three experimental runs were performed for each tested device. The results of the tests are depicted in FIG. 5. After three hours the tests with the collagen pad were repeated; no significant differences were observed in comparison to the first test results obtained (indicating that the collagen pad was essentially instantaneously hydrated).

FIG. 5 shows that a device having the collagen electrode mounting pad of the present invention has a lower impedance than a device containing a PTFE electrode mounting pad, and further exhibits impedance characteristics comparable to those of a bare electrode wire. In other words, the collagen electrode mounting pad of the present invention provides low lead system impedance, which is a highly desirable feature in a temporary atrial or ventricular defibrillation lead.

After obtaining the foregoing results, several acute implants in sheep were performed to test the feasibility of the new concept in vivo. The study's objective was to determine the DFTs of a lead made according to the present invention, and to determine whether the collagen electrode pad of the present invention was capable of preventing electrical damage to the atrial wall. In a small experiment involving only two implants in sheep, a mean DFT of 120 Volts (i.e., 0.8 Joules) was measured. No acute damage to the atrial walls was observed after shocking 10 times at 288 Volts (i.e., 5 Joules). Fixation of the electrode mounting pad onto the atrial walls was observed to be good. However, immediately after implantation the collagen pads demonstrated major shrinkage with reductions in length and width of about 50%, thereby causing partial exposure of the bare wire electrodes. Such a loss in dimensional integrity was not acceptable, and the underlying cause of the shrinkage was investigated by means of calorimetry to provide detailed information on the heat stability of the collagen material employed to form the electrode mounting pads.

When collagen is heated in a hydrated state it denatures at a specific temperature, resulting in shrinkage of the material. This shrinkage occurs as a result of the macroscopic manifestation of the transformation of collagen's native triple-helix structure to a random coil configuration. Differential scanning calorimetry (DSC) is frequently used to determine the denaturation temperature of collagen materials. DSC determines the difference in energy necessary to keep a sample pan and a reference pan at the same temperature.

The collagen obtained from Coletica to form the electrode mounting pads of the present invention was characterized using a Perkin Elmer DSC. A 5–10 mg collagen sample was placed on a 50 ml aluminum DSC sample pan having a 2 bar maximum internal pressure, after which 5 ml/mg 0.1M phosphate buffer (pH=6.88; 0.05M $Na_2HPO_4$, 0.05 M $NaH_2PO_4$) was added to hydrate the collagen. The sample pan was covered with an appropriate cover and the whole was crimp pressed. An empty sample pan was used as the reference. Typically, a run was started at 20° C. (load temperature); after 2 minutes, samples were heated to 80° C., applying a heating rate of 2° C./min. Device software was used to optimize data collection, and to calculate typical properties.

Figure 6:
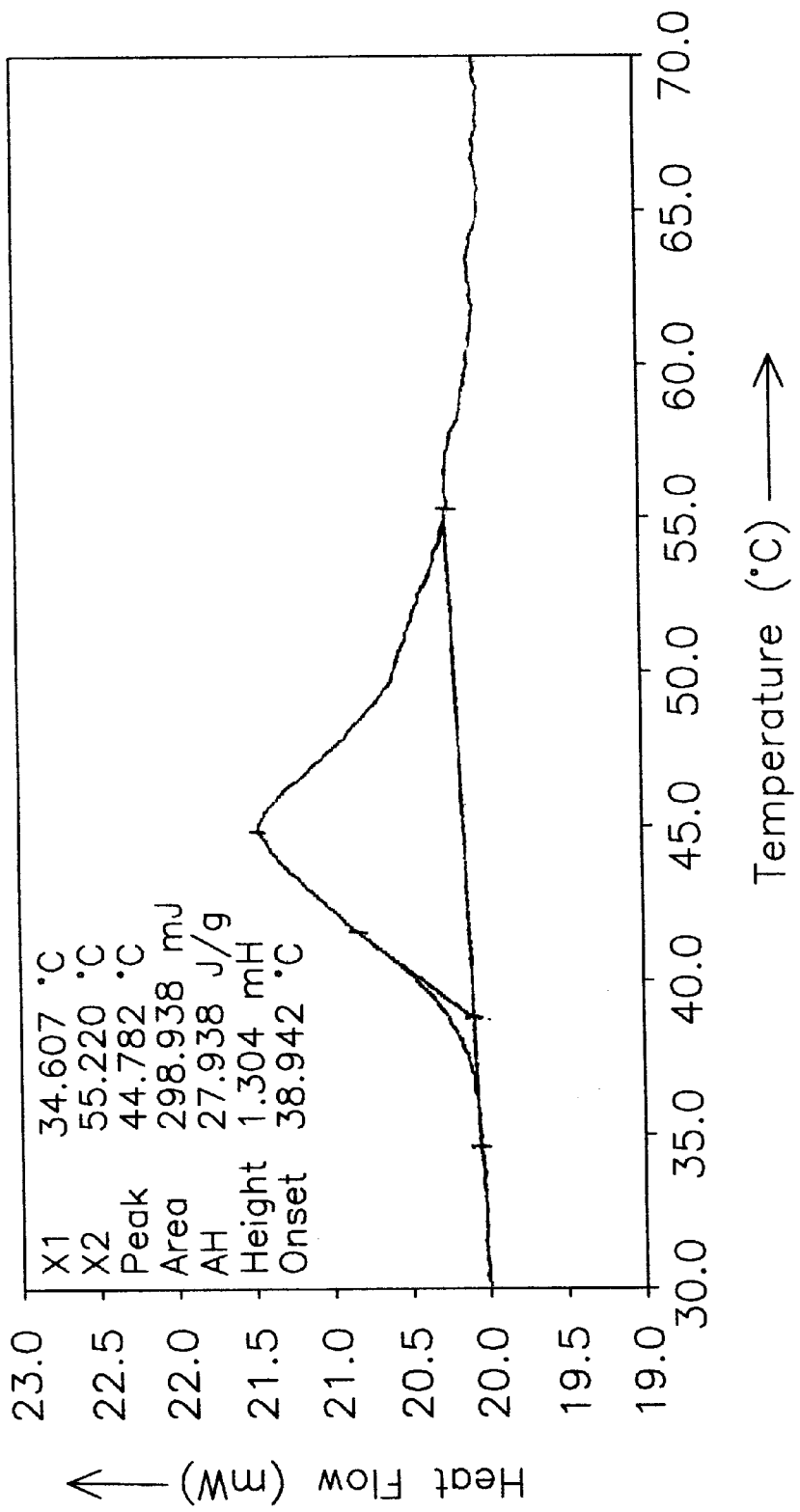
FIG. 6 shows the results of calorimetric analysis of one type of collagen material finding application in the present invention.

The resulting thermogram of FIG. 6 shows a wide peak with significant tailing. Such tailing denotes the heterogeneous character of the tested material, since short triple-helical segments more easily unwrap (or denature) than do long triple-helical segments.

Few processes exist that are suitable for sterilizing collagen products. Moist heat (or autoclaving) cannot be used to sterilize collagen because the hydrated protein is susceptible to thermal denaturation. Gaseous ethylene oxide (ETO) sterilization may be employed to sterilize collagen under moistened conditions, elevated temperatures and pressures. If the temperatures employed in ETO sterilization are not excessive, little helical denaturation occurs. Ethylene oxide reacts with the collagen. Losses of the amino acids lysine and hydroxylysine, in particular, suggest that free amino groups participate in the reaction with ethylene oxide. There is little doubt that such reactions may affect the physical and biological properties of the collagen. Consistency in the treatment and sterilization of collagen materials is therefore important.

E-beam or gamma-irradiation may also be employed to sterilize collagen products. It has, however, been shown conclusively that such methods of sterilizing collagen have a significant impact on the stability of collagen. Depending on the particular product application, therefore, irradiation/sterilization of collagen may not be appropriate.

DSC techniques were next employed to determine the relative efficacies of the three foregoing sterilization methods (i.e., ETO, E-beam and gamma-irradiation sterilization). The results obtained are shown in Table 3 below, where it becomes obvious that sterilization per se lowers the denaturation temperature of collagen material. All temperatures shown in Table 3 are in Degrees Celsius.

TABLE 3

Effect of Sterilization on Heat Stability of Collagen

| Type of Material | Peak Start Temp. | Peak End Temp. | Peak Temp. | Onset Temp.* |
|---|---|---|---|---|
| Control (non sterilized) | 36.4 | 59.9 | 44.2 | 39.6 |
| Gamma sterilized | 28.3 | 52.1 | 38.7 | 33.0 |
| E-beam sterilized | 31.3 | 50.0 | 39.4 | 35.4 |
| ETO sterilized | 35.0 | 57.1 | 40.9 | 37.2 |

*onset temperature is the temperature at which the tangent in the inflection point crosses the baseline.

As Table 3 shows, and in comparison to the control material, ETO sterilization was observed not to change the heterogeneity of the collagen material, whereas both E-beam and gamma-irradiation seem to decrease the heterogeneous character of collagen material (by exhibiting less DSC tailing). The foregoing observations in combination with the lowering of the peak start temperatures confirm that chain-scission occurs in collagen molecules, whereby shorter triple helix segments are introduced into the collagen fibers. Those shorter segments unwrap more easily during heating.

As discussed above, ETO sterilization chemically modifies collagen. The chemical modification resulting from ETO sterilization may reduce the stability of triple helix segments such that collagen denaturation is facilitated. The thermogram is of FIG. 6 shows that denaturation of ETO sterilized collagen begins at a temperature, which is below the normal body temperature of a human subject. Our calorimetric data thus help explain the findings of the first acute implant study, in which the collagen pad demonstrated major shrinkage upon contact with the atrial wall. Thus, ETO sterilization of collagen is the most preferred of the three investigated sterilization methods.

Table 4 below shows results obtained using a crosslinked collagen material, where all temperatures are in Degrees Celsius. Table 4 shows that crosslinking of collagen increases its denaturation temperature. Collagen's triple helix structure is stabilized by hydrogen bonds, which are heat unstable. Introduction of covalent crosslinks increases the stability of the triple helix, and thus increases the denaturation temperature. In the present invention, physical or chemical crosslinking methods may be employed to crosslink collagen-based materials. In addition to the increase in denaturation temperature, crosslinking also enhances the resistance to biodegradation of the material, suppresses its antigenicity and improves its mechanical properties.

As discussed above, major shrinkage of non-crosslinked collagen electrode mounting pads was observed to occur after the pads were positioned in vivo on the atrial wall. Such losses in dimensional integrity were deemed unacceptable. Crosslinking with a water-soluble carbodiimide was thus performed as a means to increase the denaturation temperature and enhance the in vivo stability of the collagen electrode mounting pad. The method of carbodiimide crosslinking was selected for its ease of operation and because carbodiimide crosslinked collagen materials generally demonstrate suitable biocompatibility properties. Our objective was to achieve an onset of the denaturation temperature slightly above body temperature between about 40° C. and about 45° C. Crosslinking specifications were set to limit the impact crosslinking would have on the biodegradation characteristics of the collagen material.

Next, calorimetry techniques were employed to permit optimization of the crosslink process. After the collagen material was exposed to various concentrations of selected crosslinking reagents, the consequent change in denaturation temperature was determined (see Table 4 below). Crosslinked materials were also ETO sterilized to determine and take into account the decrease in denaturation temperature ETO sterilization causes.

In the crosslinking process employed to acquire the data shown in Table 4 below, a collagen pad measuring about 50×30 mm and having a mass of about 0.5 grams was first hydrated in a PP beaker holding 50 ml of a 0.25 M MES buffer solution (adjusted to pH=5.0 by dropwise addition of 1N NaOH). After 30 minutes the collagen pad was withdrawn from the solution and carefully positioned on lint-free towels to permit excess buffer solution to drain away. Next, 50 ml of a 0.25M MES buffered solution (pH=5.0) containing crosslinking reagents EDC (3-ethyl-1-(diaminopropyl) carbodiimide HCl) and NHS (N-hydroxy succinimide) prepared, and within 5 minutes after adding EDC and NHS to the buffered solution the collagen pad was immersed therein. Crosslinking was permitted to proceed for 2 hours while gently shaking the buffered solution. Following crosslinking, the electrode mounting pad was first washed in distilled water three times for 15 minutes, then rinsed washed in a solution containing 0.1M $NaH_2PO_4$ for 2 hours, and then rinsed three times in distilled water for 15 minutes. Finally, the crosslinked collagen electrode mounting pad had excess water drained therefrom and was placed in a freezer at a temperature below −70° C. Once completely frozen, the collagen pad was freeze dried overnight.

TABLE 4

Effect of Crosslinking on the Heat Stability of Collagen

| | Crosslinking Level | | Peak Start | Peak End | Peak | Onset |
|---|---|---|---|---|---|---|
| Sample | EDC [:M] | NHS [;M] | Temp. | Temp. | Temp. | Temp. |
| A | 60000 | 24000 | 66.2 | 82.2 | 77.7 | 68.4 |
| B | 12000 | 12000 | 53.8 | 74.2 | 65.8 | 60.5 |
| C | 6000 | 6000 | 57.4 | 67.9 | 64.0 | 60.6 |

TABLE 4-continued

Effect of Crosslinking on the Heat Stability of Collagen

| Sample | Crosslinking Level | | Peak Start Temp. | Peak End Temp. | Peak Temp. | Onset Temp. |
| --- | --- | --- | --- | --- | --- | --- |
| | EDC [:M] | NHS [;M] | | | | |
| D | 3000 | 3000 | 56.6 | 65.4 | 61.4 | 58.7 |
| E | 1000 | 1000 | 49.2 | 65.2 | 54.7 | 50.3 |
| F | 100 | 100 | 39.9 | 65.9 | 49.9 | 44.3 |
| G | 10 | 10 | 38.6 | 65.2 | 47.6 | 42.8 |
| Control | 0 | 0 | 36.4 | 59.9 | 44.2 | 39.6 |

Figure 7:
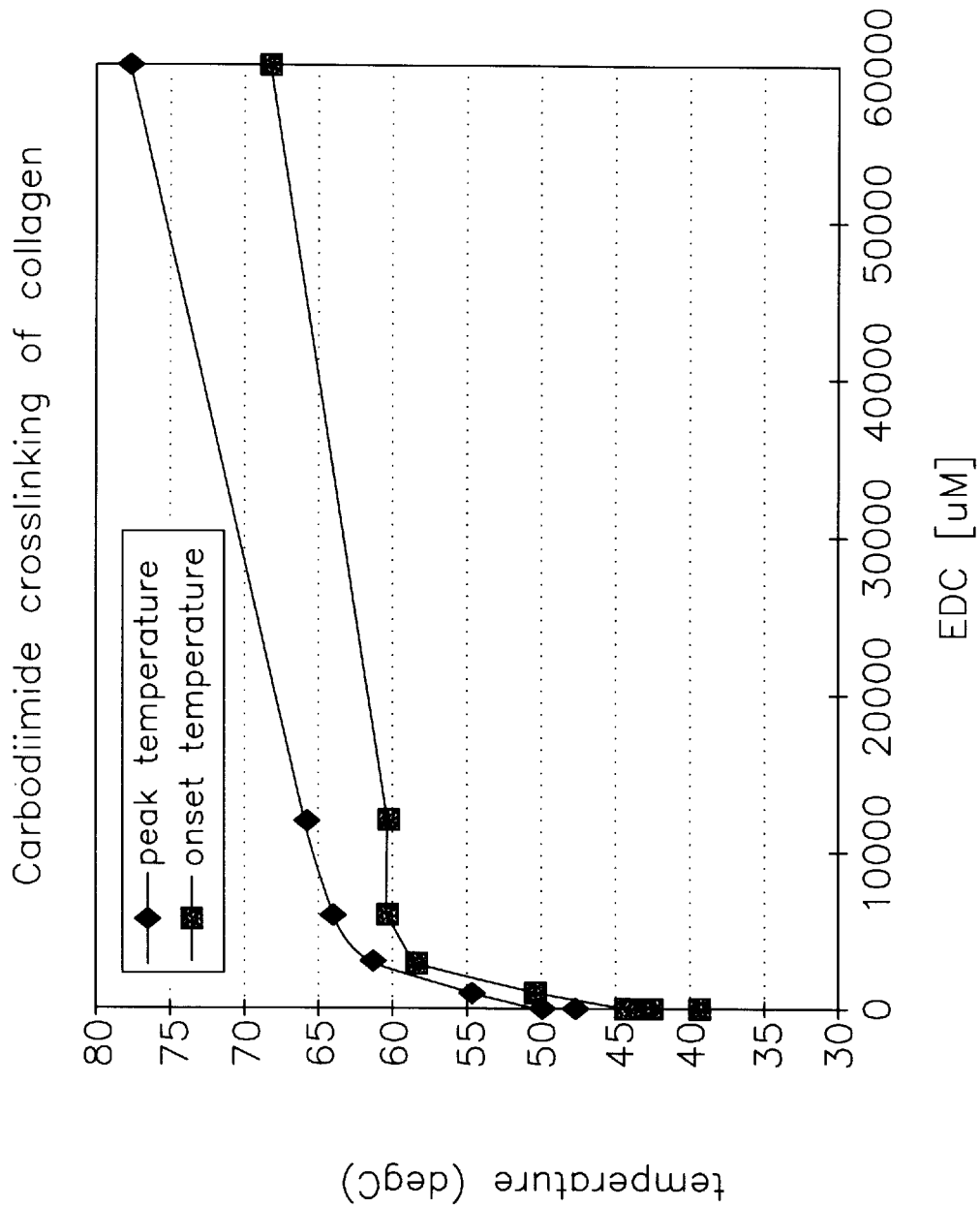
FIG. 7 shows the increase in the onset of the denaturation temperature, which occurs in a crosslinked collagen material of the present invention.

Data corresponding to Table 4 above are shown in FIG. 7, where it is shown that an immediate increase in the onset of the denaturation temperature occurs in crosslinked collagen materials of the present invention, even at low reagent concentrations. As discussed above, an increase in denaturation temperature is directly related to enhanced resistance of biodegradation.

Thus, an initial temperature ranging between about 43° C. and about 45° C. at which denaturation begins to occur was determined to provide satisfactory results in at least some embodiments of the present invention. In the light of such considerations, further experiments were conducted using collagen materials made according to the conditions and specifications corresponding to Sample F in Table 2.

Materials conforming to the conditions and specifications of Sample F were chosen over those corresponding to Sample G because ETO sterilization lowers the temperature at which the onset of denaturation occurs.

Next, the effects of ETO sterilization on crosslinked collagen electrode mounting pads was determined by calorimetric means. Table 5 below shows the results obtained, where all temperatures are in Degrees Celsius.

TABLE 5

Effect of Sterilization on Heat Stability of Collagen

| Type of Material | Peak Start Temp. | Peak End Temp. | Peak Temp. | Onset Temp. |
| --- | --- | --- | --- | --- |
| Crosslinked F (non sterilized) | 39.4 | 61.7 | 49.2 | 43.7 |
| Crosslinked F (ETO sterilized) | 38.6 | 61.7 | 48.3 | 41.6 |

In combination with the results shown in Table 4 above, Table 5 shows that crosslinking collagen electrode mounting pads using the conditions and specifications corresponding to sample F results in collagen denaturation temperatures which prevent or at the very least substantially impede in vivo shrinkage of the electrode mounting pad of the present invention.

Next we determined by in vitro collagen digestion means whether the crosslinked collagen material of the present invention made according to the optimum crosslinking techniques and parameters described above affected enzyme degradation profiles significantly in respect of non-crosslinked control collagen materials. To that end we obtained enzyme degradation profiles for non-crosslinked control collagen materials as well as for collagen materials made according to the specifications and processes corresponding to crosslinked collagen Sample F described above.

Our experimental procedures for in vitro collagen digestion were as follows. First, the weight of individual collagen strips was recorded. A collagenase stock solution was prepared, after which 5 ml aliquots were immediately frozen at a temperature below −18° C. The collagenase stock solution was a 0.1 M Tris-HCl (Sigma Chemie, Bornem, Belgium) buffered solution having a pH of 7.4, containing 5 mM $CaCl_2$ (Acros Chimica, Geel, Belgium), 0.05 mg/ml $NaN_3$ (Merck-Schuchardt, Darmstadt, Germany), and 10 U/ml collagenase (EC 3.4.24.3; from Clostridium histolyticum; type IA, 550 units/mg solid; Sigma Chemie, Bornem, Belgium). Prior to use the aliquots were thawed. Collagen strips (n=3; approx. 0.05 g) were subjected to collagenase digestion by immersion of the individual strips in 5 ml of collagenase solution at 37° C. (collagenase:collagen =1 U/mg). After 1 hour, collagenase digestion was terminated by adding 0.5 ml of 0.25 M EDTA (99%; Acros Chimica, Geel, Belgium). Thereafter, the strips were rinsed three times for 5 minutes in 0.1 M Tris-HCl having a pH of 7.4, after which the strips were rinsed a further three times for 5 minutes in distilled water. Finally, the strips were frozen for 2 hours at about −80° C. and freeze dried overnight. Thereafter, the weight of each strip was determined and the weight loss of each recorded. Digestion was continued as above until complete dissolution of the collagen strips occurred.

Figure 8:
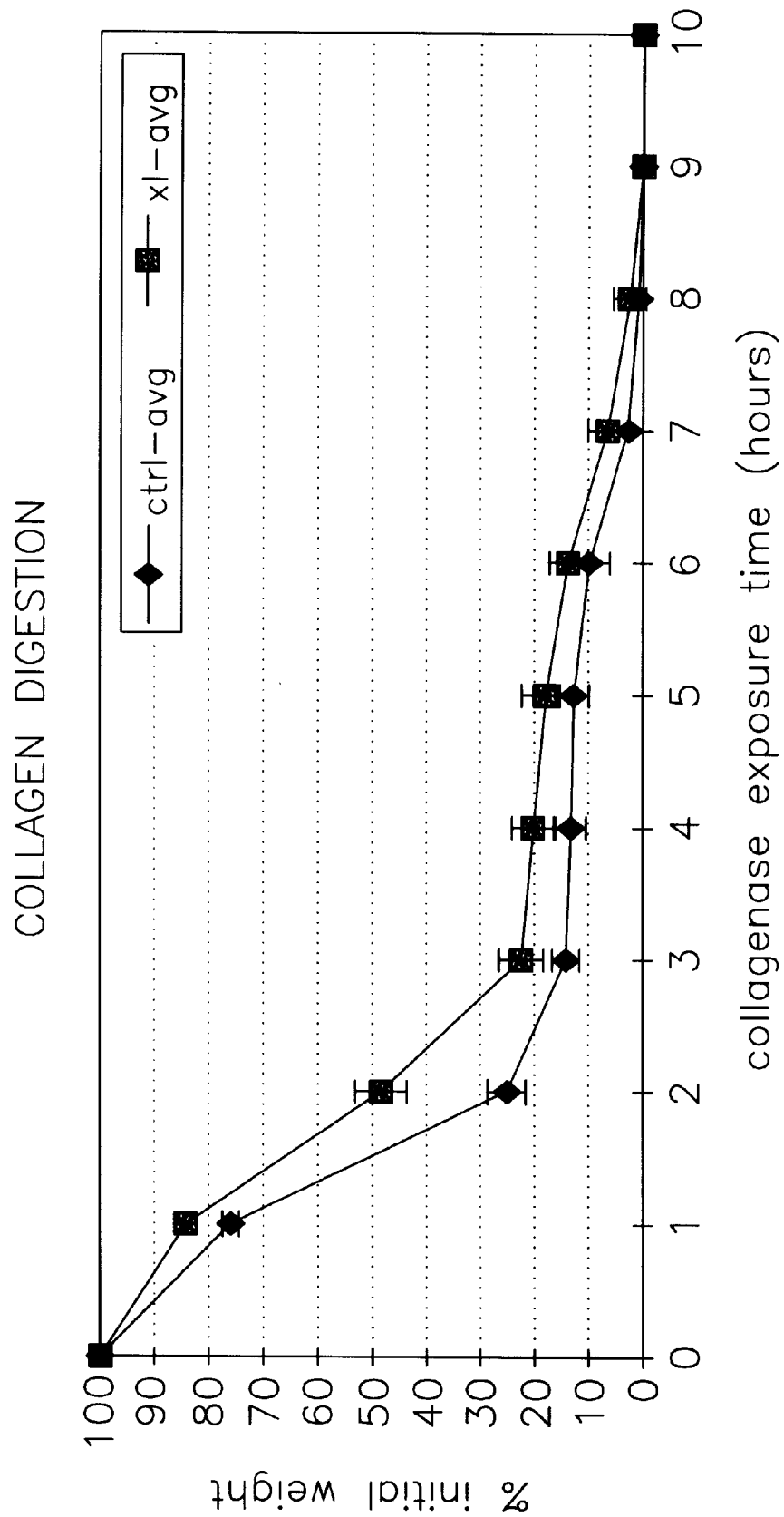
FIG. 8 shows comparative digestion profiles for crosslinked and non-crosslinked collagen materials.

FIG. 8 shows the degradation profiles obtained for the control (i.e., non-crosslinked) collagen samples and the crosslinked collagen samples made according to the conditions and specifications of Sample F. FIG. 7 shows that crosslinked collagen samples of the present invention take slightly longer to degrade than do non-crosslinked collagen samples. The increase in the amount of degradation time is very slight, however. Such a slight increase in degradation time is consistent with our initial objective of introducing a level of crosslinking in collagen, which did not appreciably affect the biodegradation characteristics of the collagen.

Another observed feature of crosslinked collagen samples in comparison to non-crosslinked samples was that degradation seemed to be changed into a surface erosion process in the crosslinked samples (as opposed to the bulk erosion processes noted in non-crosslinked samples). Unlike the early fragmentation observed in the non-crosslinked control samples, the crosslinked samples maintained their original shapes almost until the end of each experiment. Such degradation characteristics of crosslinked collagen materials may be highly advantageous in respect of maintaining the dimensional integrity of a collagen pad during the functional lifetime of an implanted temporary defibrillation lead.

In accordance with the foregoing observations and teachings, collagen electrode mounting pads appear to be much more suitable for use in temporary implantable defibrillation leads than do prior art PTFE felt electrode mounting pads. One chief advantage of the collagen electrode mounting pad of the present invention is the fact that a collagen pad is reabsorbed into the body over time so that eventually no foreign material remains in the body. Moreover, varying the degree or amount of crosslinking, which is permitted to occur in the collagen may be employed as a technique for controlling the rate at which degradation of the electrode mounting pad of the present invention proceeds when implanted within the human body.

Yet another advantage of the collagen electrode mounting pad of the present invention is the demonstrated improvement in increased conductivity (or lowered impedance) obtained with a collagen electrode mounting pad in respect of a PTFE felt electrode mounting pad. Moreover, although the conductivity of the collagen electrode mounting pad is similar to that of a bare wire, one preferred embodiment of the collagen electrode pad of the present invention helps to minimize tissue damage since the atrial wall is not permitted to directly come into contact with the defibrillation electrode (which is disposed within a matrix of surrounding collagen—see FIG. 4).

Figure 9:
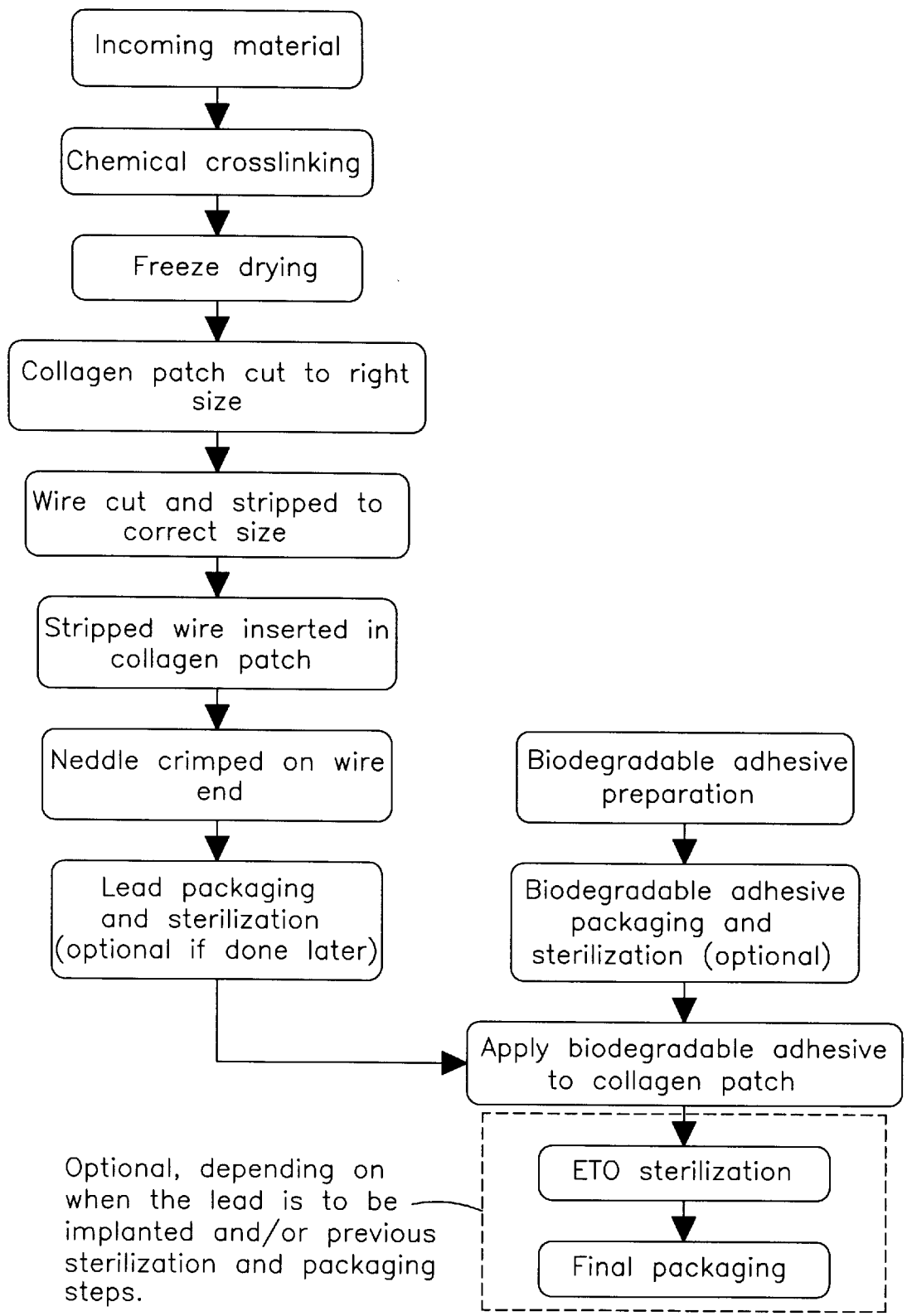
FIG. 9 illustrates one method of making a lead of the present invention.

FIG. 9 shows one method of the present invention for making a temporary defibrillation or pacing lead. After the collagen electrode mounting pad has been crosslinked, freeze dried, and cut to the proper dimensions, electrode wire/conductor 30/21 is most preferably woven through the collagen matrix using a needle. After electrode wire 30/conductor 21 has been appropriately placed in electrode mounting pad 33, break-away connector assembly 4 and its corresponding piercing needle are crimped to proximal end 4 of the lead body.

Biodegradable adhesive 15 is prepared, optionally packaged (if to be applied to the mounting pad at a later time, such as in the surgical theater, for example), and then applied to at least portions of mounting pad outer surfaces 32 or 34 (e.g., the surface which is to contact the heart). It is preferred that biodegradable adhesive 15 be applied to surface 32 or 34 which is to engage the patient's epicardium, pericardium and/or myocardium. It is also preferred, but not necessary, that sufficient amounts of biodegradable adhesive 15 be applied to surface 34 or 32 such that adhesive 15 form a substantially continuous layer thereupon so as to improve or optimize physical and electrical coupling of pad 33 and electrode wire 30/conductor 21 to heart 3. Pad 33 may be impregnated, loaded or otherwise have the biodegradable adhesive applied thereto.

In another embodiment of the present invention, no mounting pad 33 is employed. Instead, wire 30/conductor 21 is surrounded by a suitably large mass of adhesive 15, adhesive 15 being sufficiently mechanically competent and having sufficient adherent properties to retain wire 30/conductor 21 within the mass thereof, even when wire 30/conductor 21 is subjected to slight pulling or flexural forces. The mass of adhesive 15 with wire 30/conductor 21 disposed directly therewithin is configured for direct attachment to patient's heart 3. In yet another embodiment of the present invention, mounting pad 33 comprises a smaller area than that shown explicitly in the Figures hereof, or comprises a plurality of separate or connected pads, each pad most preferably, although not necessarily, being attached to wire 30/conductor 21, with adhesive 15 being disposed on at least one of the pads.

Referring now to FIG. 2, when electrode wire 30/at least one electrical conductor 21 is threaded by needle means through the collagen matrix of electrode mounting pad 33, collagen/electrode mounting pad 33 is sliced in regions A and B to permit electrode wire/conductor 21 to be re-inserted by hand into the collagen matrix in a different direction or orientation.

In another embodiment and method of the present invention, electrode wire 30/at least one electrical conductor 21 is appropriately placed and oriented in an electrode mounting cast, and a collagen-containing solution is poured therein which at least partially, if not entirely, surrounds or encases electrode wire 30/at least one electrical conductor 21. After crosslinking, dehydration and/or freeze drying processes, the collagen electrode mounting pad containing electrode 30/conductor 21 is removed from the cast and the lead is subjected to any further processing which may be required.

Figure 10:
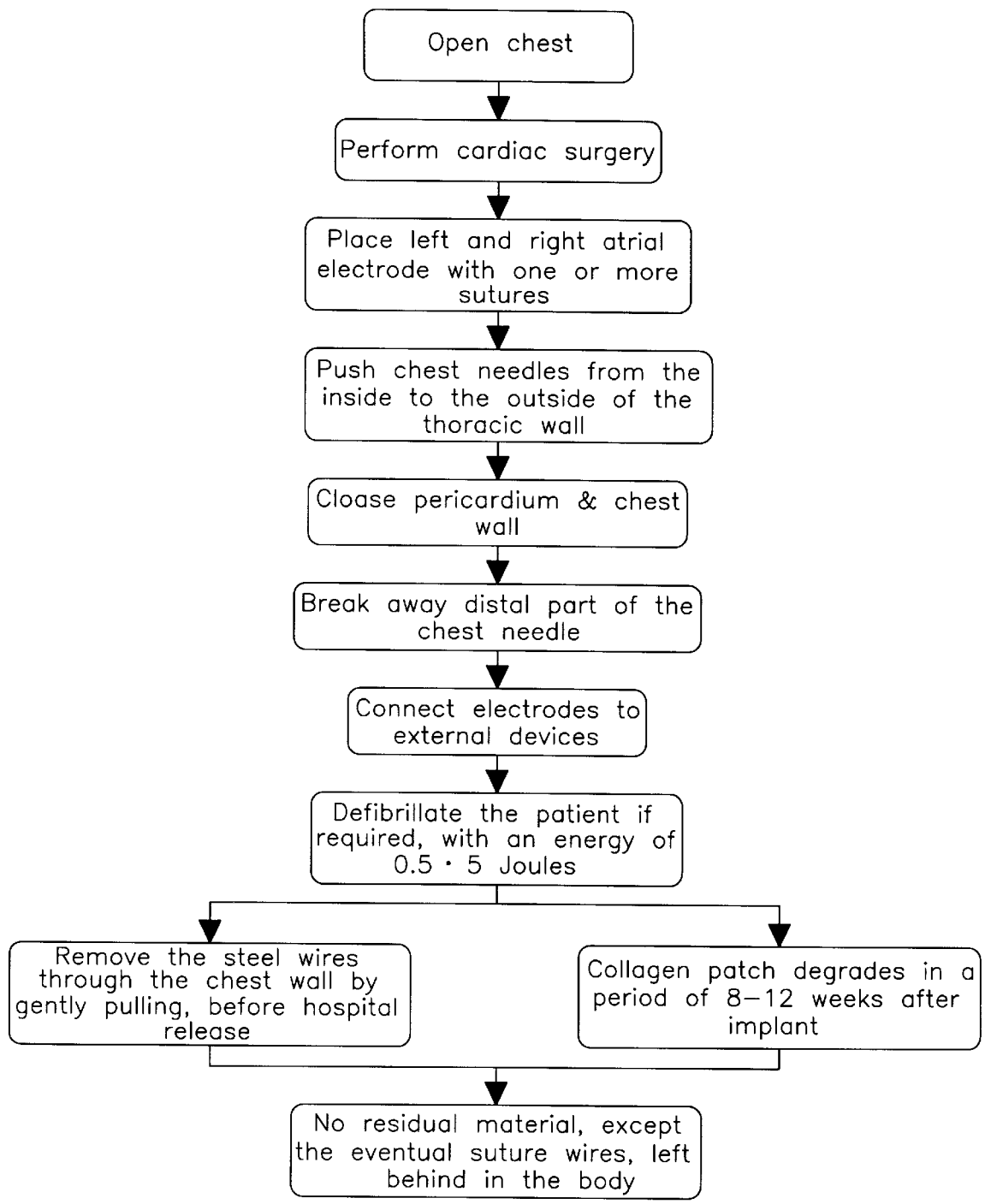
FIG. 10 illustrates one method of implanting and removing a lead of the present invention.

Referring now to FIGS. 1 and 10, in one method of the present invention implantation of lead 1 proceeds as follows. Bottom surface 32 of electrode mounting pad 33 containing suitable amounts of adhesive 15 is placed near atrium 8 on a patient's epicardium, most preferably, although not necessarily, without the use of sutures. Instead, surface 32 and/or adhesive 15 engage the epicardium, adhesive 15 forming a physical bond between the epicardium and electrode pad 33 such that pad 33 remains in the position in which it has been placed by the physician after pad 33 has been pressed onto the epicardium.

Adhesive 15 may have such a composition that it is "sticky" or provides an adherent force immediately upon being placed in contact with the epicardium. Alternatively, adhesive 15 may have a composition such that its adherent characteristics are activated, become developed, or become heightened upon being subjected to certain physical conditions which may be controlled or are known to exists at the time the lead is to be implanted. Such characteristics or conditions include a proper pH being present (e.g., the pH typically found in a patient's body fluids or tissue), a proper temperature being achieved (e.g., the internal body temperature of a patient), a separate chemical catalyst or conditioner being added to the adhesive by the physician just before pad 33 is positioned on the patient's heart (e.g., applying a buffer solution or an alkaline buffer solution to adhesive 15 just before pad 33 is implanted), and so on.

Once pad 33 has been appropriately positioned and attached to heart 3 using adhesive 15, connector assembly 4 is exteriorized at a point away from the incision through the use of a break-away needle and pin assembly known in the art (see, for example, U.S. Pat. No. 5,527,358 entitled "Temporary Medical Electrical Lead" to Mehmanesh et al.). The needle is used to pierce the skin from the interior to the exterior so as to the pin assembly. Once lead 1 is satisfactorily adhered to and/or sutured to the atrium, the pin assembly is exposed and the lead is connected to external pulse generator 2. The incision in the patient may then be closed. At this point lead 1 can deliver therapeutic electrical pulses, including defibrillating, cardioverting or pacing pulses, to atrium 8. Note that in the present invention an implantable pulse generator may be substituted for external pulse generator 2.

One important aspect of one embodiment of the lead of the present invention is the ease with which it may be removed from a patient within which it has been implanted. Conductor 21/electrode 30 is mounted within mounting pad 33 so that it may be removed, even once implanted, through the application of tractional or gentle pulling forces. That is, the distal end of conductor 21 affixed to mounting pad 33 may be gently removed therefrom through the application of a tractional force upon proximal end 5 of lead 1. Alternatively, and depending upon various factors such as the amount of time adhesive 15 and/or mounting pad 33 have been implanted within the patient and the degree of crosslinking which has been permitted to occur in mounting pad 33 or adhesive 15 during the manufacturing process, and the particular characteristics of adhesive 15, removal of conductor 21 from the patient may require the application of little tractional force owing to electrode pad 33 and adhesive 15 having been reabsorbed or dissolved in the patient's body by the time conductor 21 is pulled from the patient's body.

It will now be seen that adhesive 15 disposed in pad 33 permits quick immobilization of pad 33 during surgery, and thus results in a faster surgical procedure. The potential of damaging the patient's myocardium by suturing is thus eliminated, or in the event some sutures are employed, at least minimized or reduced. The self sticking properties of the adhesive 15 may be achieved by impregnation or coating of at least portions of pad 33 with a suitable biological substance such as, by way of example only, fibrin (in which case adhesive properties may be activated upon effecting a suitable change in pH), fibrinogen with thrombin or Factor XIII in the presence of blood, or thrombin with epsilon aminocaproic acid and $CaCl_2$, also in the presence of blood. Tissue adhesive 15 is preferably of a biological origin (e.g., human or animal) and may be prepared during surgery, or prior to surgery for storage until clinical use.

The following examples set forth various methods of preparing electrode mounting pad 33 and sticky biodegradable adhesive 15. Examples 1–3 below describe ready-made electrode pads and adhesives 15 suitable for immediate use in the surgical theater when removed from packaging. Example 4 below describes how a suitable adhesive 15 may be formed, most preferably just prior to the surgical lead implantation procedure occurring.

EXAMPLE 1

The process of making a sticky biodegradable electrode mounting pad begins with treating or impregnating pad surface 32 or 34 with an appropriate volume of Factor XIII and fibrinogen containing solution. Factor XIII and fibrinogen are obtained from fresh frozen human plasma according to well known methods. For example, 10 liters of plasma are heated to +2° C., and the cryoprecipitate containing Factor XIII and fibrinogen is obtained by centrifugation. Subsequently, the cold-soluble proteins are extracted from the cryoprecipitate by extraction with a buffer solution and removed. The remaining proteins are dissolved at 37° C., in 100 ml of a citrate-glycine buffer which contains aprotinin (2,500 KIU), heparin (20 IU) and amikacin sulfate (2,000 mg), and sterile filtered. The filtrate contains at least 1,000 units of Factor XIII and at least 7,500 mg of fibrinogen.

Electrode mounting pad 33 is treated with an appropriate volume (2 to 5 ml) of the Factor XIII and fibrinogen-containing solution. Next, electrode mounting pad 33 is frozen, lyophilized, sterilized and sterile packed. The patch is thawed prior to implantation and pressed onto the myocardium until adhesion of the patch with the myocardial tissue has occurred. See U.S. Pat. No. 4,600,574 for further details and information concerning this method.

EXAMPLE 2

The process of making a sticky biodegradable electrode mounting pad begins with treating or impregnating pad surface 32 or 43 with between about 20 and about 60 mM buffered solution of bovine thrombin and calcium chloride such that 1 to 4 IU/cm2 of bovine thrombin cover pad surface 32 or 34. In the next step, between about 60 and about 70 mg/cm2 epsilon aminocaproic acid (EACA) are applied in a sterile manner to thrombin-coated pad 33. This is followed by application of another volume of the buffered solution of bovine thrombin and calcium chloride, for example using the same concentrations as mentioned before.

Next, electrode mounting pad 33 is frozen, lyophilized, sterilized and sterile packed. Patch 33 is thawed prior to the implantation and pressed onto the myocardium until adhesion of the patch with the myocardial tissue has occurred. See U.S. Pat. No. 5,643,596 for further details and information concerning this method.

EXAMPLE 3

The process of making a sticky biodegradable electrode mounting pad begins with contacting or impregnating pad 33 with a solution comprising fibrin monomer or non-crosslinked fibrin (e.g., fibrin I or fibrin II of des BB fibrin), where the fibrin is in monomeric, oligomeric, or polymeric form, and may be converted to a crosslinked fibrin polymer.

The preparation of such fibrin has been well described in U.S. Pat. No. 5,763,411.

The solution comprising fibrin monomer or non-crosslinked fibrin is typically an aqueous solution containing up to 200 mg/ml fibrin. The aqueous solution is preferably acidic with a pH of less than 5, and a concentration of the acid buffer ranging from 0.02 M to about 1 M (and more preferably from about 0.1M to about 0.3 M).

After having applied the solution comprising fibrin monomer or non-crosslinked fibrin onto electrode mounting pad 33, pad 33 is frozen and lyophilized, sterilized and sterile packed. Patch 33 is thawed prior to implantation. Electrode mounting pad 33 coated with fibrin monomer is contacted with a suitable alkaline buffer and pressed onto the myocardium. Non-limiting examples of suitable alkaline buffers include 0.5–0.75 M Sodium carbonate/bicarbonate (pH 10–10.5), 0.5–0.75 M Sodium carbonate/NaOH (pH 10.0), or 1.5 Glycine/NaOH (pH 10.0). See U.S. Pat. No. 5,763,411 for further details and information concerning this method.

Note that in this preferred embodiment of the present invention, the fibrin monomer or non-crosslinked fibrin may be prepared in the surgical theater using a patient's own platelets to form a gel just prior to the lead implantation procedure. The gel is then employed as a component in adhesive 15. In such a preferred embodiment of adhesive 15 of the present invention, adhesive 15 is autologous.

EXAMPLE 4

The process of making a sticky biodegradable electrode mounting pad begins with contacting or impregnating pad 33 with a suitable platelet gel. This involves removing a unit of blood from a patient and separating the platelet rich plasma (PRP). The remaining blood components can be returned to the patient.

The PRP may be obtained by means of a gradient density cell separator such as the Electromedics Sequestra model separator manufactured by Medtronic, Inc. Four hundred fifty mL of autologous whole blood is withdrawn from the patient at a flow rate of 50 mL/min. with a centrifuge speed of 5600 RPM. Citrate phosphate dextrose (CPD) is added at a ratio of 1 ml of CPD to 5 mL of blood to achieve coagulation. The blood is then centrifuged into its three basic components; app. 180 mL of red blood cells, app. 70 mL of PRP (also referred to as "buffy coat"), and app. 200 mL of platelet poor plasma (PPP). The red blood cells and PPP are returned to the patient from their collection bags. This process takes about 20 to 30 minutes.

The PRP application requires initiating the coagulation process with a mixture of 10 mL of 10% calcium chloride mixed with 10,000 units of topical bovine thrombin. 6 mL of PRP, 1 mL of the calcium chloride/thrombin mix, and 1 mL of air (to act as a mixing bubble) are drawn in order into a 10 mL syringe. The syringe is agitated for 6 to 10 seconds to initiate clotting and formation of a platelet gel. The gel is added to electrode mounting pad 33. Pad 33 is pressed onto the myocardium until adhesion of the patch with the myocardial tissue has occurred. See U.S. Pat. Nos. 5,964,690 and 5,964,724 for further details and information concerning this method.

Note that in this preferred embodiment of the present invention, a patient's own platelets are employed to form a platelet gel just prior to the lead implantation procedure. The platelet gel is then employed as adhesive 15. In such a preferred embodiment of adhesive 15 of the present invention, adhesive 15 is autologous.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of any particular specific configuration of temporary defibrillation or pacing lead or electrode shown explicitly in the drawings hereof. The electrode mounting pad of the present invention need not be made of collagen, but may be formed from any other suitable biodegradable or non-biodegradable but biocompatible material. Although crosslinked collagens are preferred for the electrode mounting pad of the present invention, non-crosslinked collagen materials may also be used. Additionally, the stimulating electrode employed in conjunction with the present invention need not be a single wire or a single electrode attached to a single electrical conductor. Those skilled in the art will understand immediately that many variations and permutations of known electrical conductor/stimulating electrode configurations may be employed successfully in the present invention.

The present invention is also not limited to use in conjunction with temporary defibrillation or cardioversion leads, but may also be employed as a temporary pacing lead in bradycardia applications, as a cardiac sensing lead only, as a fetal monitoring and/or sensing lead, a fluoroless lead, a balloon lead, or a lead for use in stent implantation or other surgical procedure where cardiac backup, pacing support or defibrillation is required.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination.

All printed publications and patents referenced hereinabove are hereby incorporated by referenced herein, each in its respective entirety.

We claim:

1. A temporary medical electrical lead for pacing or defibrillating a heart of a patient, the lead having distal and proximal ends, comprising:
   (a) a lead body having proximal and distal ends, comprising:
      (i) at least one electrical conductor having proximal and distal ends;
      (ii) an insulative sheath formed of biocompatible and electrically insulative material, the sheath extending over and covering at least portions of the at least one electrical conductor;
   (b) an electrical connector assembly attached to the proximal end of the at least one electrical conductor for attachment to a device capable of providing pacing or defibrillation pulses therethrough;
   (c) an electrode mounting pad disposed near the distal end of the lead body, at least one of the distal end of the at least one electrical conductor and an electrode member secured to the distal end of the at least one electrical conductor being attached to or integrated into the electrode mounting pad, the electrode mounting pad having a lower surface for placement against the patient's myocardium, the electrode mounting pad comprising a biodegradable, biocompatible material soluble in human body fluids, and
   (d) a temporary biodegradable adhesive disposed on at least portions of the lower surface of the electrode mounting pad, the adhesive being suitable for attaching the at least portions of the lower surface to the patient's myocardium when the at least portions of the lower surface containing the adhesive are pressed against the patient's myocardium.

2. The temporary medical electrical lead of claim 3, wherein the biodegradable, biocompatible material comprises collagen.

3. The temporary medical electrical lead of claim 1, wherein the electrode mounting pad comprises a non-biodegradable material.

4. The temporary medical electrical lead of claim 1, wherein the electrode mounting pad has a thickness ranging between one of about 2 mm and about 3 mm, about 1 mm and about 4 mm, and about 0.5 mm and about 5 mm.

5. The temporary medical electrical lead of claim 1, wherein the electrical connector assembly comprises a break-away piercing needle.

6. The temporary medical electrical lead of claim 1, wherein the adhesive comprises Factor XIII and fibrinogen.

7. The temporary medical electrical lead of claim 1, wherein the adhesive comprises bovine thrombin and calcium chloride.

8. The temporary medical electrical lead of claim 1, wherein the adhesive comprises a solution containing Factor XIII and fibrinogen.

9. The temporary medical electrical lead of claim 1, wherein the adhesive comprises a fibrin monomer.

10. The temporary medical electrical lead of claim 1, wherein the adhesive comprises non-crosslinked fibrin.

11. The temporary medical electrical lead of claim 1, wherein the adhesive comprises at least one component selected from the group consisting of a monomeric fibrin polymer, an oligomeric fibrin polymer, polymeric fibrin, and a cross-linked fibrin polymer.

12. The temporary medical electrical lead of claim 1, wherein the adhesive comprises an alkaline buffer.

13. The temporary medical electrical lead of claim 1, wherein the adhesive comprises a platelet gel.

14. The temporary medical electrical lead of claim 1, wherein the adhesive comprises an autologous component.

15. A temporary medical means for electrically stimulating a heart of a patient, the stimulating means having distal and proximal ends, comprising:
   (a) a lead body having proximal and distal ends, comprising:
      (i) at least one means for conducting electricity having proximal and distal ends;
      (ii) means for electrically insulating formed of biocompatible and electrically insulative material, the insulating means extending over and covering at least portions of the at least one electrical conducting means;
   (b) an electrical means for connecting attached to the proximal end of the at least one electrical conducting means for attachment to a means for providing electrical stimulation pulses therethrough;
   (c) means for positioning a stimulating electrode near the patient's heart disposed near the distal end of the lead body, at least one of the distal end of the at least one electrical conducting means and an electrode member secured to the distal end of the at least one electrical conducting means being attached to or integrated into the electrode positioning means, the electrode positioning means having a lower surface for placement against the patient's heart, the electrode positioning means comprising a biodegradable, biocompatible material soluble in human body fluids;

(d) means for securing the electrode positioning means to the patient's myocardium, the securing means being biodegradable and disposed on at least portions of the lower surface of the electrode positioning means, the securing means being suitable for attaching the at least portions of the lower surface to the patient's myocardium when the at least portions of the lower surface containing the securing means are pressed against the patient's myocardium.

16. The temporary medical electrical lead of claim 15, wherein the biodegradable, biocompatible material comprises collagen.

17. The temporary medical electrical lead of claim 15, wherein the electrode positioning means comprises a non-biodegradable material.

18. The temporary medical electrical lead of claim 15, wherein the electrode positioning means has a thickness ranging between one of about 2 mm and about 3 mm, about 1 mm and about 4 mm, and about 0.5 mm and about 5 mm.

19. The temporary medical electrical lead of claim 15, wherein the electrical connecting means comprises a break-away means for piercing.

20. The temporary medical electrical lead of claim 15, wherein the securing means comprises Factor XIII and fibrinogen.

21. The temporary medical electrical lead of claim 15, wherein the securing means comprises bovine thrombin and calcium chloride.

22. The temporary medical electrical lead of claim 15, wherein the securing means comprises a solution containing Factor XIII and fibrinogen.

23. The temporary medical electrical lead of claim 15, wherein the securing means comprises a fibrin monomer.

24. The temporary medical electrical lead of claim 15, wherein the securing means comprises non-crosslinked fibrin.

25. The temporary medical electrical lead of claim 15, wherein the securing means comprises at least one component selected from the group consisting of a monomeric fibrin polymer, an oligomeric fibrin polymer, polymeric fibrin, and a cross-linked fibrin polymer.

26. The temporary medical electrical lead of claim 15, wherein the securing means comprises an alkaline buffer.

27. The temporary medical electrical lead of claim 15, wherein the securing means comprises a platelet gel.

28. The temporary medical electrical lead of claim 15, wherein the securing means comprises an autologous component.

29. A system for pacing or defibrillating a heart of a patient, comprising:

(a) means for generating electrical stimulating pulses suitable for delivery to the heart of the patient, and (b) an electrical lead having distal and proximal ends, comprising:

(i) a lead body having proximal and distal ends, comprising:

(1) at least one electrical conductor having proximal and distal ends;

(2) an insulative sheath formed of biocompatible and electrically insulative material, the sheath extending over and covering at least portions of the at least one electrical conductor;

(ii) an electrical connector assembly attached to the proximal end of the at least one electrical conductor for attachment to the electrical stimulating pulse generating means;

(iii) an electrode mounting pad disposed near the distal end of the lead body, at least one of the distal end of the at least one electrical conductor and an electrode member secured to the distal end of the at least one electrical conductor being attached to or integrated into the electrode mounting pad, the electrode mounting pad having a lower surface for placement against the patient's myocardium, the electrode mounting pad comprising a biodegradable, biocompatible material soluble in human body fluids, and (iv) a temporary biodegradable adhesive disposed on at least portions of the lower surface of the electrode mounting pad, the adhesive being suitable for attaching the at least portions of the lower surface to the patient's myocardium when the at least portions of the lower surface containing the adhesive are pressed against the patient's myocardium.

30. The system of claim 29, wherein the biodegradable, biocompatible material comprises collagen.

31. The system of claim 29, wherein the electrode mounting pad comprises a non-biodegradable material.

32. The system of claim 29, wherein the electrode mounting pad has a thickness ranging between one of about 2 mm and about 3 mm, about 1 mm and about 4 mm, and about 0.5 mm and about 5 mm.

33. The system of claim 29, wherein the electrical connector assembly comprises a break-away piercing needle.

34. The system of claim 29, wherein the adhesive comprises Factor XIII and fibrinogen.

35. The system of claim 29, wherein the adhesive comprises bovine thrombin and calcium chloride.

36. The system of claim 29, wherein the adhesive comprises a solution containing Factor XIII and fibrinogen.

37. The system of claim 29, wherein the adhesive comprises a fibrin monomer.

38. The system of claim 29, wherein the adhesive comprises non-crosslinked fibrin.

39. The system of claim 29, wherein the adhesive comprises at least one component selected from the group consisting of a monomeric fibrin polymer, an oligomeric fibrin polymer, polymeric fibrin, and a cross-linked fibrin polymer.

40. The system of claim 29, wherein the adhesive comprises an alkaline buffer.

41. The system of claim 29, wherein the adhesive comprises a platelet gel.

42. The system of claim 29, wherein the adhesive comprises an autologous component.

43. A method of making a temporary medical electrical lead for pacing or defibrillating a heart of a patient, the lead having distal and proximal ends and comprising a lead body having proximal and distal ends and comprising at least one electrical conductor having proximal and distal ends, an insulative sheath formed of biocompatible and electrically insulative material, the sheath extending over and covering at least portions of the at least one electrical conductor, an electrical connector assembly attached to the proximal end of the at least one electrical conductor for attachment to a device capable of providing pacing or defibrillation pulses therethrough, an electrode mounting pad disposed near the distal end of the lead body, at least one of the distal end of the at least one electrical conductor and an electrode member secured to the distal end of the at least one electrical conductor being attached to or integrated into the electrode mounting pad, the electrode mounting pad having a lower surface for placement against the patient's myocardium, the electrode mounting pad comprising a biodegradable, biocompatible material soluble in human body fluids, and a temporary biodegradable adhesive disposed on at least portions of the lower surface of the electrode mounting pad, the adhesive being suitable for attaching the at least portions of the lower surface to the patient's myocardium when the at least portions of the lower surface containing the adhesive are pressed against the patient's myocardium, the method comprising:

(a) providing the at least one electrical conductor;

(b) providing the insulative sheath;

(c) providing the electrode mounting pad;

(d) providing the connector assembly;

(e) providing the adhesive;

(f) disposing the adhesive in or on the pad, (g) disposing the insulative sheath over the at least portions of the electrical conductor;

(h) attaching the connector assembly to the proximal end of the at least one electrical conductor, and (i) attaching at least portions of the distal end of the at least one electrical conductor or of the electrode member to the electrode mounting pad.

44. The method of claim 43, wherein providing the electrode mounting pad is preceded by selecting collagen as the material from which the electrode mounting pad is formed.

45. The method of claim 43, wherein disposing the adhesive in or on the pad is preceded by including Factor XIII and fibrinogen in the adhesive.

46. The method of claim 43, wherein disposing the adhesive in or on the pad is preceded by including bovine thrombin and calcium chloride in the adhesive.

47. The method of claim 43, wherein disposing the adhesive in or on the pad is preceded by including a solution containing Factor XIII and fibrinogen in the adhesive.

48. The method of claim 43, wherein disposing the adhesive in or on the pad is preceded by including fibrin monomer in the adhesive.

49. The method of claim 43, wherein disposing the adhesive in or on the pad is preceded by including non-crosslinked fibrin in the adhesive.

50. The method of claim 43, wherein disposing the adhesive in or on the pad is preceded by including at least one component selected from the group consisting of a monomeric fibrin polymer, an oligomeric fibrin polymer, polymeric fibrin, and a cross-linked fibrin polymer, in the adhesive.

51. The method of claim 43, wherein disposing the adhesive in or on the pad is followed by including an alkaline buffer in the adhesive.

52. The method of claim 43, wherein disposing the adhesive in or on the pad is preceded by including a platelet gel in the adhesive.

53. The method of claim 43, wherein disposing the adhesive in or on the pad is preceded by including an autologous component in the adhesive.

54. A method of implanting a medical electrical lead for pacing or defibrillating a heart of a patient, the lead having distal and proximal ends and comprising a lead body having proximal and distal ends and comprising at least one electrical conductor having proximal and distal ends, an insulative sheath formed of biocompatible and electrically insulative material, the sheath extending over and covering at least portions of the at least one electrical conductor, an electrical connector assembly attached to the proximal end of the at least one electrical conductor for attachment to a device capable of providing pacing or defibrillation pulses therethrough, an electrode mounting pad disposed near the distal end of the lead body, at least one of the distal end of the at least one electrical conductor and an electrode member secured to the distal end of the at least one electrical conductor being attached to or integrated into the electrode mounting pads the electrode mounting pad having a lower surface for placement against the patient's myocardium, the electrode mounting pad comprising a biodegradable, biocompatible material soluble in human body fluids, and a temporary biodegradable adhesive disposed on at least portions of the lower surface of the electrode mounting pad, the adhesive being suitable for attaching the at least portions of the lower surface to the patient's myocardium when the at least portions of the lower surface containing the adhesive are pressed against the patient's myocardium, the method comprising:

(a) at least partially securing the electrode mounting pad to the heart of the patient with the adhesive, (b) connecting the connector assembly to the means for generating electrical stimulating pulses;

(c) providing electrical stimulating pulses to the heart with the electrode or the distal end of the electrical conductor and the electrical stimulating pulse generating means;

(f) permitting the adhesive to dissolve in body fluids of the patient.

55. A temporary medical electrical lead for pacing or defibrillating a heart of a patient, the lead having distal and proximal ends, comprising:

(a) a lead body having proximal and distal ends, comprising:

(i) at least one electrical conductor having proximal and distal ends;

(ii) an insulative sheath formed of biocompatible and electrically insulative material, the sheath extending over and covering at least portions of the at least one electrical conductor;

(b) an electrical connector assembly attached to the proximal end of the at least one electrical conductor for attachment to a device capable of providing pacing or defibrillation pulses therethrough;

(c) a temporary biodegradable adhesive disposed near the distal end of the lead body, at least one of the distal end of the at least one electrical conductor and an electrode member secured to the distal end of the at least one electrical conductor being attached to, integrated into, or disposed within or on the adhesive, the adhesive being suitable for attaching the at least portions of the lower surface to the patient's myocardium when at least portions of the adhesive are pressed against the patient's myocardium.

* * * * *

UNITED STATES PATENT AND TRADEMARK OFFICE
CERTIFICATE OF CORRECTION

PATENT NO.    : 6,463,335 B1
DATED         : October 8, 2002
INVENTOR(S)   : Münch et al.

It is certified that error appears in the above-identified patent and that said Letters Patent is hereby corrected as shown below:

<u>Column 22,</u>
Line 11, change "electrical lead of claim 3" to -- electrical lead of claim 1 --.

Signed and Sealed this

Third Day of June, 2003

JAMES E. ROGAN
*Director of the United States Patent and Trademark Office*